(12) United States Patent
Jia et al.

(10) Patent No.: US 7,695,743 B2
(45) Date of Patent: *Apr. 13, 2010

(54) FORMULATION OF A MIXTURE OF FREE-B-RING FLAVONOIDS AND FLAVANS FOR USE IN THE PREVENTION AND TREATMENT OF COGNITIVE DECLINE AND AGE-RELATED MEMORY IMPAIRMENTS

(75) Inventors: Qi Jia, Olympia, WA (US); Bruce Burnett, Hollywood, FL (US); Yuan Zhao, Olympia, WA (US)

(73) Assignee: Unigen Pharmaceuticals, Inc., Lacey, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/962,363

(22) Filed: Dec. 21, 2007

(65) Prior Publication Data

US 2008/0096827 A1    Apr. 24, 2008

Related U.S. Application Data

(63) Continuation of application No. 10/932,571, filed on Sep. 1, 2004, now abandoned, and a continuation-in-part of application No. 10/427,746, filed on Apr. 30, 2003, now Pat. No. 7,514,469.

(60) Provisional application No. 60/499,742, filed on Sep. 2, 2003, provisional application No. 60/377,168, filed on Apr. 30, 2002.

(51) Int. Cl.
    *A01N 65/00* (2009.01)
(52) U.S. Cl. ....................................... 424/725
(58) Field of Classification Search ........................ None
    See application file for complete search history.

(56) References Cited

U.S. PATENT DOCUMENTS

| 3,686,872 | A | 8/1972 | Whitworth et al. |
| 3,706,581 | A | 12/1972 | Whitworth et al. |
| 4,268,517 | A | 5/1981 | Niebes |
| 4,374,824 | A | 2/1983 | Wahmi |
| 4,515,804 | A | 5/1985 | Marti et al. |
| 4,946,684 | A | 8/1990 | Blank et al. |
| 5,443,983 | A | 8/1995 | Ochoa et al. |
| 5,470,589 | A | 11/1995 | Shi |
| 5,545,411 | A | 8/1996 | Chancellor |
| 5,605,929 | A | 2/1997 | Liao et al. |
| 5,643,598 | A | 7/1997 | Maybeck |
| 5,650,432 | A | 7/1997 | Walker |
| 5,650,433 | A | 7/1997 | Watanabe et al. |
| 5,651,987 | A | 7/1997 | Fuisz |
| 5,756,538 | A | 5/1998 | Cassels et al. |
| 5,795,911 | A | 8/1998 | Cheng et al. |
| 5,858,371 | A | 1/1999 | Singh et al. |
| 5,886,029 | A | 3/1999 | Dhaliwal |
| 5,886,155 | A | 3/1999 | Armah et al. |
| 5,922,756 | A | 7/1999 | Chan |
| 5,962,517 | A | 10/1999 | Murad |
| 5,968,973 | A | 10/1999 | Cheng et al. |
| 6,080,401 | A | 6/2000 | Reddy et al. |
| 6,083,921 | A | 7/2000 | Xu |
| 6,093,403 | A | 7/2000 | Huo et al. |
| 6,126,940 | A | 10/2000 | Takahashi et al. |
| 6,126,950 | A | 10/2000 | Bindra et al. |
| 6,197,808 | B1 | 3/2001 | Cheng et al. |
| 6,217,875 | B1 | 4/2001 | Murai et al. |
| 6,235,294 | B1 | 5/2001 | Perrier et al. |
| 6,248,341 | B1 | 6/2001 | Anderson et al. |
| 6,264,995 | B1 | 7/2001 | Newmark et al. |
| 6,280,751 | B1 | 8/2001 | Fletcher et al. |
| 6,290,995 | B1 | 9/2001 | Xinxian |
| 6,387,416 | B1 | 5/2002 | Newmark et al. |
| 6,391,346 | B1 | 5/2002 | Newmark et al. |
| 6,475,530 | B1 | 11/2002 | Kuhrts |
| 6,555,573 | B2 | 4/2003 | Rosenbloom |
| 7,045,158 | B2 | 5/2006 | Wolfson et al. |
| 7,108,868 | B2 | 9/2006 | Jia et al. |
| 7,192,611 | B2 | 3/2007 | Jia et al. |
| 7,514,469 | B2 | 4/2009 | Jia |

(Continued)

FOREIGN PATENT DOCUMENTS

CN    1096680 A    12/1994

(Continued)

OTHER PUBLICATIONS

Mayo Clinic, Alzheimer's disease, 2 pages, 2009.*
Afolayan and Meyer (1997) Journal of Ethnopharmacol. 57(3):177-181.
Agarwal et al. (1993) Photochem. Photobiol. 58:695-700.
Amos et al. (1999) Phytotherapy Research 13:683-685.
Ardlie et al. (1985) Thromb. Res. 38(6):695-706.
Bastianetto et al. (2000) Br. J. Pharmacol. 131:711-720.
Bickford et al. (1999) Free Rad. Biol. Med. 26:817-8245.
Bickford et al. (1999) Mech. Ageing Dev. 111:141-154.
Bickford et al. (2000) Brain. Res. 866:211-217.

(Continued)

*Primary Examiner*—Michael V Meller
(74) *Attorney, Agent, or Firm*—Swanson & Bratschun, L.L.C.

(57) ABSTRACT

The present invention provides a novel method for preventing and treating memory and cognitive impairment resulting from oxidative stress, inflammation and the process of aging, as well as, neurodegenerative conditions. The method is comprised of administering a composition comprising a mixture of Free-B-Ring flavonoids and flavans synthesized and/or isolated from a single plant or multiple plants to a host in need thereof. The present also includes a novel method for simultaneously inhibiting expression of pro-inflammatory cytokines, preventing ROS generation and augmenting anti-oxidant defenses. The activity of this composition is conducive to ultimately preserving cognitive function and providing a level of neuroprotection.

8 Claims, 19 Drawing Sheets

U.S. PATENT DOCUMENTS

| | | | |
|---|---|---|---|
| 7,531,521 | B2 | 5/2009 | Burnett et al. |
| 2001/0026813 | A1 | 10/2001 | Kim et al. |
| 2001/0046963 | A1 | 11/2001 | Wenzel et al. |
| 2002/0086070 | A1 | 7/2002 | Kuhrts |
| 2002/0122836 | A1 | 9/2002 | Obukowicz et al. |
| 2002/0136784 | A1 | 9/2002 | Obukowicz et al. |
| 2003/0105030 | A1 | 6/2003 | Liao et al. |
| 2003/0166583 | A1 | 9/2003 | Yoa-Pu Hu et al. |
| 2005/0049206 | A1 | 3/2005 | Gong et al. |
| 2006/0269627 | A1 | 11/2006 | Jia et al. |
| 2007/0135359 | A1 | 6/2007 | Jia |
| 2007/0264361 | A1 | 11/2007 | Jo et al. |

FOREIGN PATENT DOCUMENTS

| | | |
|---|---|---|
| CN | 1043406 C | 5/1999 |
| CN | 1285202 A | 2/2001 |
| EP | 0742012 A2 | 11/1996 |
| EP | 0956867 A1 | 11/1999 |
| FR | 2651132 | 3/1991 |
| GB | 2306321 | 5/1997 |
| JP | 403240725 | 10/1991 |
| JP | 07010768 | 1/1995 |
| JP | 407017847 | 1/1995 |
| JP | 7223941 | 8/1995 |
| JP | H08-104628 A | 4/1996 |
| JP | 9227374 | 9/1997 |
| JP | 2001-220353 | 8/2001 |
| JP | 2002053484 | 2/2002 |
| WO | WO 98/19651 | 5/1998 |
| WO | WO 98/40086 | 9/1998 |
| WO | WO 98/42363 | 10/1998 |
| WO | WO 98/49256 | 11/1998 |
| WO | WO 00/59523 | 10/2000 |
| WO | WO 00/67749 | 11/2000 |
| WO | WO 02/09699 | 2/2002 |
| WO | WO 02/42429 | 5/2002 |
| WO | WO 02/47615 | 6/2002 |

OTHER PUBLICATIONS

Boumendjel et al. (2001) Bioorg. Med. Chem. Lett. 11(1):75-77.
Brideau et al. (1996) Inflamm. Res. 45:68-74.
Butenko et al. (1993) Agents Actions Special Conference Issue 39:C49-C51.
Butterfield et al. (1998) Ann. NY Acad. Sci. 854:448-462.
Cao et al. (1999) J. Applied Physiol. 86:1817-1822.
Carney et al. (May 1991) Proc. Natl. Acad. Sci. USA 88:3633-3636.
Cartford et al. (Jul. 15, 2002) J. Neurosci. 22:5813-5816.
Chen et al. (2001) Biochem. Pharmacol. 61(11):1417-1427.
Chen et al., Oroxylin A inhibition of lipopolysaccharide-induced iNOS and COX-2 gene expression via suppression of nuclear factor-kappaB activation (Jun. 1, 2000) Biochemical Pharmacology 59:1445-1447.
Chi et al. (2001) Biochem. Pharmacol. 61:1195-1203.
Chinese Herbs Direct, 2007, pp. 1-2, www.chinneseherbsdirect.com.
Chung et al., Pharmacological Effects of Methanolic Extract from the Root of Scutellaria baicalensis and its Flavonoids on Human Gingival Fibroblast (Apr. 1995) Planta Med. 61:150-153.
Commenges et al. (Apr. 2000) Eur. J. Epidemiol 16:357-363.
Dafallah and Al-Mustafa (1996) American Journal of Chinese Medicine. 24:263-269.
de la Puerta et al. (1999) Planta Medica 65:507-511.
de Whalley et al. (1990) Biochemical Pharmacology 39:1743-1750.
Gemma et al. (Jul. 15, 2002) J. Neurosci. 22(4):6114-6120.
Gilani et al. (Dec. 1999) Phytotherapy Research. 13:665-669.
Gould et al. (1998) Neurosci. Lett. 250:165-168.
Hagos et al. (Feb. 1987) Planta Medica. 53:27-31, 1987.
Hanausek-Walaszek et al. (Mar. 2000) Proceedings American Association for Cancer Research Annual Meeting 41:663 (abstract #4216).
Haridas et al. (Mar. 2000) Proceedings American Association for Cancer Research Annual Meeting. 41:600 (abstract #3820).
Heo et al. (2001) Mutat. Res. 488(2):135-150.
Heo et al., J. Agric. Food Chem, 52, 13, 4128-4132, 2004, abstract only.
Hong et al. (2001) Biochemical Pharmacology 62:1175-1183.
Imamura et al. (2000) J. Biochem. 127(4):653-658.
Itoigawa et al. (1999) J. Ethnopharmacol. 65(3): 267-272.
Kalkbrenner et al. (1992) Pharmacology 44(1):1-12.
Kaneko and Baba (1999) Biosci Biotechnol. Biochem 63(2):323-328.
Kikukawa et al. (1995) Ensho 15(2):129-33 (Abstract).
Kim et al. (1990) Yakhak Hoeji 34(5):348-364.
Kimura et al. (2001) Planta Med. 67:331-334.
Krakauer et al. (2001) FEBS Lett. 500:52-55.
Kubo et al. (1984) Chemical and Pharmaceutical Bulletin 32(7):2724-2729.
Kubo et al. (2000) Bioorg. Med. Chem. 8(7):1749-1755.
Kuhn et al. (1988) Biomed Biochim. Acta, 47:S320-S323.
Lee et al. (1998) Cancer Lett. 132:219-227.
Lenton and Greenstock (1999) Mech. Ageing Dev. 107:15-20.
Li et al. (2000) Immunopharmacology 49:295-306.
Liang et al. (2001) FEBS Lett. 496(1):12-18.
Lynch (1998) Prog. Neurobiol. 56:571-589.
Meyer et al. (1997) J. Ethnopharmacol. 56(2):165-169.
Min et al. (1999) Planta Med. 65:460-462.
Montine et al. (2003) Biochem. Pharmacol. 65:611-617.
Moroney et al. (1988) J. Pharm. Pharmacol. 40:787-792.
Murray and Lynch (May 15, 1998) J. Biol. Chem. 273:12161-12168.
Mutoh et al. (Jul. 2000) Jnp. J. Cancer Res. 91:686-691.
Nadkarni (1996) India Materia Medica, Bombay Popular Prakashan, pp. 9-17.
Nakagami (Aug. 22, 1995) Database WPI Week 199519 Aug. 22, 1995, Derwent Publications Ltd., London, GB; p. 2, AN 1995-325471 XP002418722 Nakagami T; Nakamura T; Tamura N: "Anti-complementary substance used as therapeutic agent—comprises gallic acid, methyl gallate, acetyl-salicylic acid, caffeic acid, catechin, epi-gallo-catechin gallate, myricetin, quercitrin and/or baicalein, or their salts" (abstract).
Nakahata et al. (1998) Am. J. Chin Med. 26:311-323 (abstract).
Nakahata et al. (1999) Nippon Yakurigaku Zasshi 114, Supp. 1:215P-219P.
Nakajima et al. (2001) Planta Med. 67(2):132-135.
Noreen et al. (1998) Planta Med. 64:520-524.
Noreen et al. (Jan. 1998) J. Nat. Prod. 61:2-7.
Noreen et al. (Jan. 1998) J. Nat. Prod. 61:8-12.
Park et al. (2001) Biochem. Biophys. Res. Commun. 286:721-725.
Raso et al. (2001) Life Sci. 68(8):921-931.
Salmon et al. (1985) Prostaglandins 29(3):377-385.
Sekine et al. (1997) Chemical and Pharmaceutical Bulletin. 45:148-11.
Shah et al. (1997) General Pharmacology. 29:251-255.
So et al. (1997) Cancer Lett. 112(2):127-133.
Sobottka et al. (2000) Arch. Pharm. Pharm. Med. Chem. 333:205-210.
Stadtman and Berlett (1998) Drug Metab. Rev. 30:225-243.
Sugiyama, Yakushigaku Zasshi, 2005, 40(2), 98-106, abstract only.
Tordera et al. (Mar.-Apr. 1994) Z. Naturforsch [C] 49:235-240 abstract only.
Wakabayashi and Yasui (2000) Eur. J. Pharmacol. 406(3):477-481.
Wang (Mar. 2000) Phytomedicine 7:15-19.
Wenzel et al. (Jul. 2000) Cancer Res. 60:3823-3831.
Whiteman and Halliwell (1996) Free Rad. Res. 25:275-283.
Yamahara et al. (1981) Shoyakugaku Zasshi 35(2):103-107 (Abstract).
Yang et al. (1999) J. Nutr. Sci. Vitaminol. 45:337-346.
Yoshimura et al. (2002) Free Rad. Res. 36:107-112.
You et al. (1999) Arch. Pharm. Res. 22:18-24.
2004 International Congress on Natural Products Research, Phoenix, Arizona, Jul. 31-Aug. 4, 2004, Gafner et al., Evaluation of the anti-inflammatory properties of skullcap (*Scutellaria lateriflora* L.) extracts in different in vitro models, p. 60 and poster.

Hukkeri et al. (Dec. 1, 2002) Indian Drugs 39(12):664-666, "Anti-inflammatory activity of leaves of *Acadia farnesiana willd*".

Office Action issued Jan. 10, 2007 in related U.S. Appl. No. 10/932,571.

Office Action issued Jun. 27, 2007 in related U.S. Appl. No. 10/932,571.

Office Action issued Jan. 2, 2009 in related U.S. Appl. No. 11/927,061.

Office Action issued Feb. 26, 2009 in U.S. Appl. No. 11/661,382.

Office Action issued Jun. 15, 2009 in U.S. Appl. No. 11/279,925.

\* cited by examiner

| Gene | Subject #1 | Subject #2 | Subject #3 | Average |
|---|---|---|---|---|
| cox1 | 3 | -3 | -5 | -1.7 |
| cox2 | -71 | -84 | -35 | -63 |
| il-1β | -108 | -11 | -16 | -45 |
| tnfα | -6 | -1.5 | -2.5 | -3.3 |
| il-6 | nd | -40 | -34 | -37 |
| pparγ | nd | -7 | -13 | -10 |
| nfκb | -2.7 | -2.2 | -1.6 | -2.2 |

FIG. 14

FORMULATION OF A MIXTURE OF FREE-B-RING FLAVONOIDS AND FLAVANS FOR USE IN THE PREVENTION AND TREATMENT OF COGNITIVE DECLINE AND AGE-RELATED MEMORY IMPAIRMENTS

RELATED APPLICATIONS

This application is a continuation of U.S. application Ser. No. 10/932,571, filed Sep. 1, 2004, entitled "Formulation Of A Mixture Of Free-B-Ring Flavonoids And Flavans For Use In The Prevention And Treatment Of Cognitive Decline And Age-Related Memory Impairments", which claims the benefit of U.S. Provisional Application Ser. No. 60/499,742, filed Sep. 2, 2003, entitled "Formulation with dual COX-2 and 5-lipoxygenase inhibitory activity for use in the prevention and treatment of cognitive decline and age-related memory impairments." This application is also a continuation in part of U.S. application Ser. No. 10/427,746, filed Apr. 30, 2003, which claims the benefit of U.S. Provisional Application Ser. No. 60/377,168, filed Apr. 30, 2002, each of which is entitled "Formulation With Dual Cox-2 And 5-Lipoxygenase Inhibitory Activity." Each of these applications is incorporated herein by reference in its entirety.

FIELD OF THE INVENTION

This invention relates generally to a composition of matter formulated for use in the prevention and treatment of neurodegradation, neuroinflammation and cumulative cognitive declines, disorders, diseases and conditions resulting from exposure to reactive oxygen species (ROS), inflammatory proteins and eicosanoids. Specifically, the present invention relates to a novel composition of matter comprised of a mixture of a blend of two specific classes of compounds—Free-B-Ring flavonoids and flavans—for use in the prevention and treatment of age, cognitive, neuroinflammatory and neurodegenerative related diseases and conditions mediated by oxidative insult, inflammation and the cycloxygenase (COX) and lipoxygenase (LOX) pathways. The diseases and conditions include, but are not limited to, neurodegenerative disorders, stroke, dementia, Alzheimer's disease, Parkinson's disease, Huntington's disease, Amyotrophic Lateral Sclerosis (ALS) and cognitive declines resulting from advancing age.

BACKGROUND OF THE INVENTION

The liberation and metabolism of arachidonic acid (AA) from the cell membrane results in the generation of pro-inflammatory metabolites by several different pathways. Arguably, two of the most important pathways to inflammation are mediated by the enzymes 5-lipoxygenase (5-LO) and cycloxygenase (COX). These parallel pathways result in the generation of leukotrienes and prostaglandins, respectively, which play important roles in the initiation and progression of the inflammatory response. These vasoactive compounds are chemotaxins, which promote infiltration of inflammatory cells into tissues and serve to prolong the inflammatory response. Consequently, the enzymes responsible for generating these mediators of inflammation have become the targets for many new drugs aimed at the treatment of inflammation that contributes to the pathogenesis of diseases such as rheumatoid arthritis, osteoarthritis, Alzheimer's disease and certain types of cancer.

Inhibition of the COX enzyme is the mechanism of action attributed to most nonsteroidal anti-inflammatory drugs (NSAIDS). There are two distinct isoforms of the COX enzyme (COX-1 and COX-2) that share approximately 60% sequence homology, but differ in expression profiles and function. COX-1 is a constitutive form of the enzyme that has been linked to the production of physiologically important prostaglandins involved in the regulation of normal physiological functions such as platelet aggregation, protection of cell function in the stomach and maintenance of normal kidney function (Dannhardt and Kiefer (2001) Eur. J. Med. Chem. 36:109-126). The second isoform, COX-2, is a form of the enzyme that is inducible by pro-inflammatory cytokines such as interleukin-1β (IL-1β) and other growth factors (Herschmann (1994) Cancer Metastasis Rev. 134:241-256; Xie et al. (1992) Drugs Dev. Res. 25:249-265). This isoform catalyzes the production of prostaglandin E2 ($PGE_2$) from AA. Inhibition of COX-2 is responsible for the anti-inflammatory activities of conventional NSAIDs.

Inhibitors that demonstrate dual specificity for COX-2 and 5-LO, while maintaining COX-2 selectivity relative to COX-1, would have the obvious benefit of inhibiting multiple pathways of AA metabolism. Such inhibitors would block the inflammatory effects of prostaglandins (PG), as well as, those of multiple leukotrienes (LT) by limiting their production. This includes the vasodilation, vasopermeability and chemotactic effects of $PGE_2$, LTB4, LTD4 and LTE4, also known as the slow reacting substance of anaphalaxis. Of these, LTB4 has the most potent chemotactic and chemokinetic effects. (Moore (1985) in *Prostanoids: Pharmacological, Physiological and Clinical Relevance*, Cambridge University Press, N.Y., pp. 229-230.

In addition to the above-mentioned benefits of dual COX-2/5-LO inhibitors, many dual inhibitors do not cause some of the side effects that are typical of NSAIDs or COX-2 inhibitors, including both the gastrointestinal damage and discomfort caused by traditional NSAIDs. It has been suggested that NSAID-induced gastric inflammation is largely due to metabolites of 5-LO, particularly LTB4, which attracts cells to the site of a gastric lesion thus causing further damage. (Kircher et al. (1997) Prostaglandins Leukot. Essent. Fatty Acids 56:417-423). Leukotrienes represent the primary AA metabolites within the gastric mucosa following prostanoid inhibition. It appears that these compounds contribute to a significant amount of the gastric epithelial injury resulting from the use of NSAIDs. (Celotti and Laufer (2001) Pharmacological Research 43:429-436). Dual inhibitors of COX and 5-LO were also demonstrated to inhibit the coronary vasoconstriction in arthritic hearts in a rat model. (Gok et al. (2000) Pharmacology 60:41-46). Taken together, these characteristics suggest that there may be distinct advantages to dual inhibitors of COX-2 and 5-LO over specific COX-2 inhibitors and non-specific NSAIDs with regard to both increased efficacy and reduced side effects.

Because the mechanism of action of COX inhibitors overlaps that of most conventional NSAIDs, COX inhibitors are used to treat many of the same symptoms, such as the pain and swelling associated with inflammation in transient conditions and chronic diseases in which inflammation plays a critical role. Transient conditions include the treatment of inflammation associated with minor abrasions, sunburn or contact dermatitis, as well as, the relief of pain associated with tension and migraine headaches and menstrual cramps. Chronic conditions include arthritic diseases such as rheumatoid arthritis and osteoarthritis. Although rheumatoid arthritis is largely an autoimmune disease and osteoarthritis is caused by the degradation of cartilage in joints, reducing the inflammation associated with each provides a significant increase in the quality of life for those suffering from these diseases (Wienberg (2001) Immunol. Res. 22:319-341; Wollhiem (2000)

Curr. Opin. Rheum. 13:193-201). As inflammation is a component of rheumatic diseases in general, the use of COX inhibitors has been expanded to include diseases such as systemic lupus erythromatosus (SLE) (Goebel et al. (1999) Chem. Res. Tox. 12:488-500; Patrono et al. (1985) J. Clin. Invest. 76:1011-1018) and rheumatic skin conditions such as scleroderma. COX inhibitors are also used for the relief of inflammatory skin conditions that are not of rheumatic origin, such as psoriasis, in which reducing the inflammation resulting from the over production of prostaglandins could provide a direct benefit (Fogh et al. (1993) Acta Derm. Venereol (Oslo) 73:191-193).

Recent scientific progress has identified correlations between COX-2 expression, general inflammation and the pathogenesis of Alzheimer's disease (AD). (Ho et al. (2001) Arch. Neurol. 58:487-92). In animal models, transgenic mice that over-express the COX-2 enzyme have neurons that are more susceptible to damage. The National Institute on Aging (NIA) is launching a clinical trial to determine whether NSAIDs can slow the progression of Alzheimer's disease. Naproxen (a non-selective NSAID) and rofecoxib (Vioxx, a COX-2 specific selective NSAID) will be evaluated. Previous evidence has indicated that inflammation contributes to Alzheimer's disease. According to the Alzheimer's Association and the NIA, about 4 million people suffer from AD in the United States and this is expected to increase to 14 million by mid-century.

The protective effect of NSAIDs in the pathogenesis of AD is attributed to COX-2 inhibition and the direct prevention of amyloidosis in the brain. (Xiang et al. (2002) Gene Expression 10:271-278). By suppressing COX-2 production of the pro-inflammatory prostaglandin $PGE_2$, the surrounding neurons are also spared from the oxidative and inflammatory insult that would be generated by activated microglia. (Combs et al. (2001) Neurochem. Intl. 39:449-457). This action eliminates the subsequent microglial generation of cytokines and ROS that feed the cycle and propagate neurodegeneration. (Kalaria et al. (1996) Neurodegeneration 5:497-503; Combs et al. (1999) J. Neurosci. 19:928-939). NSAIDs also inhibit γ-secretase activity thereby preventing amyloid precursor protein (APP) processing, elevation of amyloid-beta (Aβ) peptide levels and development of neurofibrillary tangles (NFT) and neuritic plaque (Weggen et al. (2001) Nature 414:212-216; Takahashi et al. (2003) J. Biol. Chem. 278:18664-18670).

The progressive neural deterioration resulting from exposure to ROS, cytokines and pro-inflammatory eicosanoids manifests itself in a number of disease states all of which share common roots. These diseases are currently treated with NSAIDs which have cognitive preserving and neuroprotective properties resulting from their multifactoral activity on ROS, cytokines and pro-inflammatory eicosanoids. They act to inhibit amyloid deposition, diminish thromboxane and prostanoid production, attenuate cytokine production, prevent microglial activation, lower ROS generation, and, in some instances, possess a high antioxidant capacity. All of these activities can prevent cognitive decline and slow the cumulative effect upon neurodegeneration resulting from oxidative stress and aging.

The neuroprotective activity of NSAID's forms the basis of current theories regarding somatic and neurodegenerative decline seen with varying degenerative disease states, aging, inflammation and oxidative stress. Initial observations that exposure to ionizing radiation mimics some of these conditions by causing similar histopathological changes in irradiated organs and their antioxidant status implicated the generation of free radicals as a causal factor. (Gerschman et al. (1954) Science 119:623-626; Harman (1956) J. Gerontol. 11:289-300; Harman (1957) J. Gerontol. 2:298-300). Administration of antioxidants prior to exposure provided the organism with some protection against the damaging effects of radiation. The conclusion derived from these studies was that prolonged exposure to free radical oxidative stress generated by ionizing radiation or oxidative metabolism disturbs the REDOX balance of the intracellular environment and is damaging in and of itself, if not held in check through antioxidant defenses. From this observation arose the leading studies on increasing longevity and neuroprotection, involving the lowering of free radical levels through manipulating basal metabolism via caloric restriction. (Berg and Simms (1960) J. Nutr. 71: 255-261; Weindruch and Walford (1988) *The retardation of aging and disease by dietary restriction*. C. C. Thomas, Springfield, Ill.).

Berg and Simms proposed that maintenance of somatic function was correlated with restricted caloric intake and the subsequent reduced production of free radicals via oxidative metabolism, essentially, caloric restriction (CR). (Berg and Simms (1960) J. Nutr. 71: 255-261). Harman suggested that this protection, through the use of antioxidants, would extend to the nervous system by preventing lipid peroxidation. (Harman (1969) J. Gerontol. 23:476-482). Other investigators observed that cellular and DNA damage appeared to be roughly correlated to the organism's basal metabolic rate (BMR) and demonstrated that the higher the BMR, the shorter the lifespan and the greater the cellular and DNA damage. (Barja (2002) Free Rad. Biol. Med. 33:1167-1172). The explanation being that the generation of destructive ROS from mitochondrial and cytoplasmic oxidative metabolism produces an accumulation of free radical-induced damage at both the cellular and molecular level and is responsible, in part, for numerous degenerative and age-related disorders. The damage caused by ROS, however, can be reduced by suppressing BMR via CR or by augmenting antioxidant defenses to compete with ROS production. CR has repeatedly been shown to be an effective method to increase the longevity of a number of species. (Weindruch and Walford (1988) *The retardation of aging and disease by dietary restriction*, C. C. Thomas, Springfield, Ill.; Weindruch (1989) Prog. Clin. Biol. Res. 287:97-103). This research has lead to an invigorated examination of the antioxidant status of the organism with respect to progressive somatic and neurodeterioration seen with aging and the subsequent development of a free radical theory of aging. (Harman (1994) Ann. NY Acad. Sci. 717:1-15).

Additional studies, which demonstrate neuroprotective activity associated with augmentation or supplementation of an organism's antioxidant defenses, support this theory. Dietary supplementation in rodents with micronutrients (Liu et al. (2002) Ann. NY Acad. Sci. 959:133-166), antioxidants (Floyd and Hensley (2000) Ann. NY Acad. Sci. 899:222-237; Joseph et al. (2000) Mech. Ageing Dev. 116:141-153; Galli et al. (2002) Ann. NY Acad. Sci. 959:128-132) and plant extracts (Bickford et al. (2000) Brain. Res. 866:211-217; Cartford et al. (2002) J. Neurosci. 22:5813-5816) were shown to protect the aging nervous system against ionizing radiation (Lenton and Greenstock (1999) Mech. Ageing Dev. 107:15-20) or oxidative insult (Butterfield et al. (1998) Ann. NY Acad. Sci. 854:448-462; Cao et al. (1999) J. Applied Physiol. 86:1817-1822), in addition to improving behavior in cognitive tasks (Bickford et al. (1999) Mech. Ageing Dev. 111: 141-154) and restoring CNS electrophysiological responses (Gould et al. (1998) Neurosci. Lett. 250:165-168; Bickford et al. (1999) Free Rad. Biol. Med. 26:817-824). All of these intervention therapies are presumed to alter the antioxidant status of the intracellular milieu and protect key cytoplasmic and mitochondrial contents from degradation by ROS, thereby restoring and/or preserving homeostasis. Indices of antioxidant status have shown corresponding changes with these dietary manipulations. For example, lipid peroxide markers, malondialdehyde (MDA) (Gemma et al. (2002) J. Neurosci. 22:6114-6120) and hydroxynonenal (HNE) are lowered (Yoshimura et al. (2002) Free Rad. Res. 36:107-112), isoprostanes are decreased (Montine et al. (2003) Biochem. Pharmacol. 65:611-617), 8-hydroxy-2-deoxyguanosine levels are reduced (Lee et al. (1998) Cancer Lett. 132:219-227), protein carbonyls (Carney et al. (1991) Proc. Natl. Acad. Sci. USA 88:3633-3636; Stadtman and Berlett (1998) Drug Metab. Rev. 30:225-243) and nitrotyrosine residues drop (Whiteman and Halliwell (1996) Free Rad. Res. 25:275-283), and spin trapping antioxidants show lowered reactivity (Carney et al. (1991) Proc. Natl. Acad. Sci. USA 88:3633-3636).

Treatment with the spin-trapping antioxidant N-tert-butyl-α-phenylnitrone (PBN) demonstrates the ability to pharmacologically attenuate neurodegeneration induced by aging and ROS. PBN is a free radical scavenger, which has been shown to decrease ROS (Floyd (1999) Proc Soc Exp Biol Med. 222(3):236-245.), lower protein carbonyl generation in the senescence accelerated mouse model (Butterfield et al. (1997) Proc. Natl. Acad. Sci. USA 94:674-678), protect the brains of gerbils in ischemia re-perfusion injuries (Floyd and Hensley (2000) Ann. NY Acad. Sci. 899:222-237), preserve cerebellar responsiveness in aged rats (Gould and Bickford (1994) Brain Res. 660:333-336), and decrease the rate of telomere shortening in human fibroblasts (von Zglinicki et al. (2000) Free Rad. Biol. Med. 28:64-74). PBN has also proven effective in lowering protein carbonyl content in aged gerbils and improving their performance in the radial arm maze behavioral task. (Carney et al. (1991) Proc. Natl. Acad. Sci. USA 88:3633-3636). It remains, therefore, a compelling proposition to augment an organism's antioxidant defenses by various nutritional interventions.

Aging and oxidative stress are associated with declines in hippocampal processing of information (Barnes (1990) Prog. Brain Res. 86:89-104; McGahon et al. (1997) Neuroscience 81:9-16; Murray and Lynch (1998a) J. Neurosci. 273:12161-12168), as demonstrated by the deficits seen in spatial learning, memory formation and the decline in Long Term Potentiation (LTP), which is necessary for memory consolidation. The composition of matter disclosed herein, which is a COX and LOX inhibitor, as well as, a strong antioxidant can reduce declines in hippocampal processing resulting from oxidative stress, inflammation or aging.

Lastly, inflammatory prostanoids compromise LTP by up-regulating the inflammatory cytokine IL-1β. This cytokine, which has been shown to increase with age and oxidative stress, inhibits LTP in the CA1 region of the hippocampus and the DG. (Murray and Lynch (1998a) J. Neurosci. 273:12161-12168). Associated with the up-regulation in IL-1β expression is an increase in lipid peroxidation in the hippocampus. (Murray et al. (1999) Gerontology 45:136-142). Further evaluation of this process revealed that animals treated with an antioxidant rich diet experienced a reversal of age-related changes in IL-1β, lipid peroxidation and the associated deficit in LTP. (Lynch (1998) Prog. Neurobiol. 56:571-589). Additionally, the age-related decrease in membrane AA concentration was also ameliorated by dietary supplementation with an antioxidant. (Murray and Lynch (1998b) J. Biol. Chem. 273:12161-12168). All of these factors clearly indicate that cognitive declines resulting from exposure to oxidative stress, inflammation and aging can be slowed or ameliorated by dietary and pharmacological interventions.

Flavonoids or bioflavonoids are a widely distributed group of natural products, which have been reported to have antibacterial, anti-inflammatory, antiallergic, antimutagenic, antiviral, antineoplastic, anti-thrombic and vasodilatory activity. The structural unit common to this group of compounds includes two benzene rings on either side of a 3-carbon ring as illustrated by the following general structural formula:

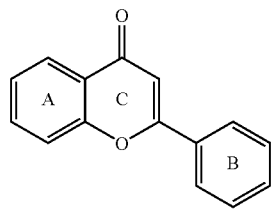

Various combinations of hydroxyl groups, sugars, oxygen and methyl groups attached to this general three ring structure create the various classes of flavonoids, which include flavanols, flavones, flavan-3-ols (catechins), anthocyanins and isoflavones.

The intake of flavonoids has been demonstrated to be inversely related to the risk of incident dementia. The mechanism of action, while not known, has been speculated as being due to the anti-oxidative effects of flavonoids. (Commenges et al. (2000) Eur. J. Epidemiol. 16:357-363). Polyphenol flavones induce programmed cell death, differentiation and growth inhibition in transformed colonocytes by acting at the mRNA level on genes including cox-2, Nuclear Factor kappa B (NFκB) and bcl-X(L). (Wenzel et al. (2000) Cancer Res. 60:3823-3831). It has been reported that the number of hydroxyl groups on the B ring is important in the suppression of cox-2 transcriptional activity. (Mutoh et al. (2000) Jnp. J. Cancer Res. 91:686-691).

Recent reports have addressed the possible involvement of flavonoids, isolated from the medicinal herb *Scutellaria baicalensis*, in alterations in cox-2 gene expression. (Wakabayashi and Yasui (2000) Eur. J. Pharmacol. 406(3):477-481; Chen et al. (2001) Biochem. Pharmacol. 61:1417-1427; Chi et al. (2001) Biochem. Pharmacol. 61:1195-1203; Raso et al. (2001) Life Sci. 68(8):921-931). The term gene expression is often used to describe both mRNA production and protein synthesis. In fact, changes in actual gene expression may never result in observable changes in protein levels. The corollary, that changes in protein levels do not always result from changes in gene expression, can also be true. There are six possible points of regulation in the pathway leading from genomic DNA to a functional protein: (1) transcriptional regulation by nuclear factors and other signals leading to production of pre-mRNA; (2) pre-mRNA processing regulation involving exon splicing, the additions of a 5' cap structure and 3' poly-adenylation sequence and transport of the mature mRNA from the nucleus into the cytoplasm; (3) mRNA transport regulation controlling localization of the mRNA to a specific cytoplasmic site for translation into protein; (4) mRNA degradation regulation controlling the size of the mRNA pool either prior to any protein translation or as a means of ending translation from that specific mRNA; (5) translational regulation of the specific rate of protein translation initiation and (6) post-translation processing regulation involving modifications such as glycosylation and proteolytic cleavage. In the context of genomics research it is important to use techniques that measure gene expression levels closer to the initial steps (e.g. mRNA levels), rather than the later steps (e.g. protein levels) in this pathway.

Each of above cited studies related to cox-2 gene expression use a Western Blot technique, for protein analysis, to evaluate putative alterations in gene expression without validation on the DNA or mRNA levels. Since the Western Blot technique measures only protein levels and not the specific transcription product, mRNA, it is possible that other mechanisms are involved leading to the observed increase in protein expression. For example, LPS has been reported to modulate mRNA half-lives via instability sequences found in the 3' untranslated region (3'UTR) of mRNAs (Watkins et al. (1999) Life Sci. 65:449-481), which could account for increased protein expression without alternations in the rate of gene transcription. Consequently, this leaves open the question of whether or not these treatment conditions resulted in a meaningful change in gene expression.

Techniques such as RT-qPCR and DNA microarray analysis rely on mRNA levels for analysis and can be used to evaluate levels of gene expression under different conditions, i.e. in the presence or absence of a pharmaceutical agent. To date Applicant is unaware of any reported methods that specifically measure the amount of mRNA, directly or indirectly, when a composition comprised of a combination of Free-B-ring flavonoids and flavans are used as the therapeutic agents.

Free-B-Ring flavones and flavonols are a specific class of flavonoids, which have no substituent groups on the aromatic B ring (referred to herein as Free-B-Ring flavonoids), as illustrated by the following general structure:

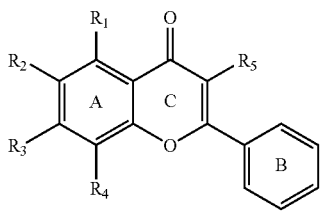

wherein $R_1$, $R_2$, $R_3$, $R_4$, and $R_5$ are independently selected from the group consisting of —H, —OH, —SH, OR, —SR, —NH$_2$, —NHR, —NR$_2$, —NR$_3^+$X$^-$, a carbon, oxygen, nitrogen or sulfur, glycoside of a single or a combination of multiple sugars including, but not limited to aldopentoses, methyl-aldopentose, aldohexoses, ketohexose and their chemical derivatives thereof;

wherein

R is an alkyl group having between 1-10 carbon atoms; and

X is selected from the group of pharmaceutically acceptable counter anions including, but not limited to hydroxyl, chloride, iodide, fluoride, sulfate, phosphate, acetate, carbonate, etc.

Free-B-ring flavonoids are relatively rare. Out of 9,396 flavonoids synthesized or isolated from natural sources, only 231 Free-B-ring flavonoids are known (*The Combined Chemical Dictionary*, Chapman & Hall/CRC, Version 5:1 Jun. 2001). Free-B-ring flavonoids have been reported to have diverse biological activity. For example, galangin (3,5,7-trihydroxyflavone) acts as an anti-oxidant and free radical scavenger and is believed to be a promising candidate for antigenotoxicity and cancer chemoprevention. (Heo et al. (2001) Mutat. Res. 488:135-150). It is an inhibitor of tyrosinase monophenolase (Kubo et al. (2000) Bioorg. Med. Chem. 8:1749-1755), an inhibitor of rabbit heart carbonyl reductase (Imamura et al. (2000) J. Biochem. 127:653-658), has antimicrobial activity (Afolayan and Meyer (1997) Ethnopharmacol. 57:177-181) and antiviral activity (Meyer et al. (1997) J. Ethnopharmacol. 56:165-169). Baicalein and two other Free-B-ring flavonoids, have antiproliferative activity against human breast cancer cells. (So et al. (1997) Cancer Lett. 112:127-133).

Typically, flavonoids have been tested for biological activity randomly based upon their availability. Occasionally, the requirement of substitution on the B-ring has been emphasized for specific biological activity, such as the B-ring substitution required for high affinity binding to p-glycoprotein (Boumendjel et al. (2001) Bioorg. Med. Chem. Lett. 11(1): 75-77); cardiotonic effect (Itoigawa et al. (1999) J. Ethnopharmacol. 65(3): 267-272), protective effect on endothelial cells against linoleic acid hydroperoxide-induced toxicity (Kaneko and Baba (1999) Biosci Biotechnol. Biochem 63(2): 323-328), COX-1 inhibitory activity (Wang (2000) Phytomedicine 7:15-19) and prostaglandin endoperoxide synthase (Kalkbrenner et al. (1992) Pharmacology 44(1):1-12). Only a few publications have mentioned the significance of the unsubstituted B ring of the Free-B-Ring flavonoids. One example is the use of 2-phenyl flavones, which inhibit NADPH quinone acceptor oxidoreductase, as potential anticoagulants. (Chen et al. (2001) Biochem. Pharmacol. 61(11): 1417-1427).

The mechanism of action relative to the anti-inflammatory activity of various Free-B-Ring flavonoids has been controversial. The anti-inflammatory activity of the Free-B-Ring flavonoids, chrysin (Liang et al. (2001) FEBS Lett. 496(1): 12-18), wogonin (Chi et al. (2001) Biochem. Pharmacol. 61:1195-1203) and halangin (Raso et al. (2001) Life Sci. 68(8):921-931), has been associated with the suppression of inducible cycloxygenase and nitric oxide synthase via activation of peroxisome proliferator activated receptor gamma (PPARγ) and influence on degranulation and AA release. (Tordera et al. (1994) Z. Naturforsch [C] 49:235-240). It has been reported that oroxylin, baicalein and wogonin inhibit 12-lipoxygenase activity without affecting cycloxygenase. (You et al. (1999) Arch. Pharm. Res. 22(1):18-24). More recently, the anti-inflammatory activity of wogonin, baicalin and baicalein has been reported as occurring through inhibition of inducible nitric oxide synthase and cox-2 gene expression induced by nitric oxide inhibitors and lipopolysaccharide. (Chen et al. (2001) Biochem. Pharmacol. 61(11):1417-1427). It has also been reported that oroxylin acts via suppression of NFκB activation. (Chen et al. (2001) Biochem. Pharmacol. 61(11):1417-1427). Finally, wogonin reportedly inhibits inducible PGE$_2$ production in macrophages. (Wakabayashi and Yasui (2000) Eur. J. Pharmacol. 406(3):477-481).

Inhibition of the phosphorylation of mitrogen-activated protein kinase and inhibition of Ca$^{2+}$ ionophore A23187 induced PGE$_2$ release by baicalein has been reported as the mechanism of anti-inflammatory activity of Scutellariae radix. (Nakahata et al. (1999) Nippon Yakurigaku Zasshi, 114, Supp. 11:215 P-219P; Nakahata et al. (1998) Am. J. Chin Med. 26:311-323). Baicalin from *Scutellaria baicalensis*, reportedly inhibits superantigenic staphylococcal exotoxins stimulated T-cell proliferation and production of IL-1β, IL-6, TNF-α, and interferon-γ (IFN-γ). (Krakauer et al. (2001) FEBS Lett. 500:52-55). Thus, the anti-inflammatory activity of baicalin has been associated with inhibiting the pro-inflammatory cytokines mediated signaling pathways activated by superantigens. However, it has also been postulated that the anti-inflammatory activity of baicalin is due to the binding of a variety of chemokines, which limits their biological activity. (Li et al. (2000) Immunopharmacology 49:295-306). Recently, the effects of baicalin on adhesion molecule expression induced by thrombin and thrombin receptor agonist peptide (Kimura et al. (2001) Planta Med. 67:331-334), as well as, the inhibition of mitogen-activated protein kinase cascade (MAPK) (Nakahata et al. (1999) Nippon Yakurigaku Zasshi, 114, Supp 11:215 P-219P; Nakahata et al. (1998) Am. J. Chin Med. 26:311-323) have been reported.

The Chinese medicinal plant, *Scutellaria baicalensis* contains significant amounts of Free-B-Ring flavonoids, including baicalein, baicalin, wogonin and baicalenoside. Traditionally, this plant has been used to treat a number of conditions including clearing away heat, purging fire, dampness-warm and summer fever syndromes; polydipsia resulting from high fever; carbuncle, sores and other pyogenic skin infections; upper respiratory infections, such as acute tonsillitis, laryngopharyngitis and scarlet fever; viral hepatitis; nephritis; pelvitis; dysentery; hematemesis and epistaxis. This plant has also traditionally been used to prevent miscarriage. (*Encyclopedia of Chinese Traditional Medicine*, ShangHai Science and Technology Press, ShangHai, China, 1998). Clinically *Scutellaria* is now used to treat conditions such as pediatric pneumonia, pediatric bacterial diarrhea, viral hepatitis, acute gallbladder inflammation, hypertension, topical acute inflammation, resulting from cuts and surgery, bronchial asthma and upper respiratory infections. (*Encyclopedia of Chinese Traditional Medicine*, ShangHai Science and Technology Press, ShangHai, China, 1998). The pharmacological efficacy of *Scutellaria* roots for treating bronchial asthma is reportedly related to the presence of Free-B-Ring flavonoids and their suppression of eotaxin associated recruitment of eosinophils. (Nakajima et al. (2001) Planta Med. 67(2):132-135).

To date, a number of naturally occurring Free-B-Ring flavonoids have been commercialized for various uses. For example, liposome formulations of *Scutellaria* extracts have been utilized for skin care. (U.S. Pat. Nos. 5,643,598; 5,443, 983). Baicalin has been used for preventing cancer, due to its inhibitory effects on oncogenes. (U.S. Pat. No. 6,290,995). Baicalin and other compounds have been used as antiviral, antibacterial and immunomodulating agents (U.S. Pat. No. 6,083,921 and WO98/42363) and as natural anti-oxidants (WO98/49256 and Poland Pub. No. 9,849,256). *Scutellaria baicalensis* root extract has been formulated as a supplemental sun screen agent with additive effects of the cumulative SPFs of each individual component in a topical formulation (WO98/19651). Chrysin has been used for its anxiety reducing properties (U.S. Pat. No. 5,756,538). Anti-inflammatory flavonoids are used for the control and treatment of anorectal and colonic diseases (U.S. Pat. No. 5,858,371), and inhibition of lipoxygenase (U.S. Pat. No. 6,217,875). These compounds are also formulated with glucosamine collagen and other ingredients for repair and maintenance of connective tissue (U.S. Pat. No. 6,333,304). Flavonoid esters constitute active ingredients for cosmetic compositions (U.S. Pat. No. 6,235, 294). U.S. application Ser. No. 10/091,362, filed Mar. 1, 2002, entitled "Identification of Free-B-Ring Flavonoids as Potent COX-2 Inhibitors," and U.S. application Ser. No. 10/427,746, filed Apr. 30, 2003, entitled "Formulation With Dual Cox-2 And 5-Lipoxygenase Inhibitory Activity," both disclose a method for inhibiting the cycloxygenase enzyme COX-2 by administering a composition comprising a Free-B-Ring flavonoid or a composition containing a mixture of Free-B-Ring flavonoids to a host in need thereof. This is the first report of a link between Free-B-Ring flavonoids and COX-2 inhibitory activity. These applications are specifically incorporated herein by reference in their entirety.

Japanese Pat. No. 63027435, describes the extraction, and enrichment of baicalein and Japanese Pat. No. 61050921 describes the purification of baicalin.

Flavans include compounds illustrated by the following general structure:

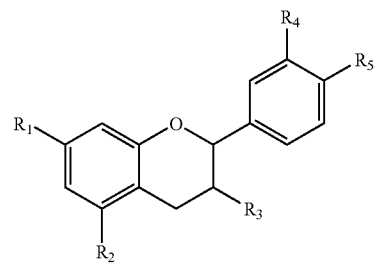

wherein $R_1$, $R_2$, $R_3$, $R_4$ and $R_5$ are independently selected from the group consisting of —H, —OH, —SH, —OCH$_3$, —SCH$_3$, —OR, —SR, —NH$_2$, —NRH, —NR$_2$, —NR$_3^+$X$^-$, esters of the mentioned substitution groups, including, but not limited to, gallate, acetate, cinnamoyl and hydroxyl-cinnamoyl esters, trihydroxybenzoyl esters and caffeoyl esters, and their chemical derivatives thereof; a carbon, oxygen, nitrogen or sulfur glycoside of a single or a combination of multiple sugars including, but not limited to, aldopentoses, methyl aldopentose, aldohexoses, ketohexose and their chemical derivatives thereof; dimer, trimer and other polymerized flavans;

wherein

R is an alkyl group having between 1-10 carbon atoms; and

X is selected from the group of pharmaceutically acceptable counter anions including, but not limited to hydroxyl, chloride, iodide, sulfate, phosphate, acetate, fluoride, and carbonate, etc.

Catechin is a flavan, found primarily in green tea, having the following structure:

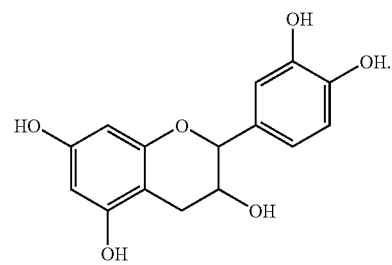

Catechin

Catechin works both alone and in conjunction with other flavonoids found in tea, and has both antiviral and antioxidant activity. Catechin has been shown to be effective in the treatment of viral hepatitis. It also appears to prevent oxidative damage to the heart, kidney, lungs and spleen and has been shown to inhibit the growth of stomach cancer cells.

Catechin and its isomer epicatechin inhibit prostaglandin endoperoxide synthase with an IC$_{50}$ value of 40 μM. (Kalkbrenner et al. (1992) Pharmacol. 44:1-12). Five flavan-3-ol derivatives, including (+)-catechin and gallocatechin, isolated from four plant species: *Atuna racemosa*, *Syzygium carynocarpum*, *Syzygium malaccense* and *Vantanea peruviana*, exhibit equal to weaker inhibitory activity against COX- 2, relative to COX-1, with $IC_{50}$ values ranging from 3.3 μM to 138 μM. (Noreen et al. (1998) Planta Med. 64:520-524). (+)-Catechin, isolated from the bark of *Ceiba pentandra*, inhibits COX-1 with an $IC_{50}$ value of 80 μM. (Noreen et al. (1998) J. Nat. Prod. 61:8-12). Commercially available pure (+)-catechin inhibits COX-1 with an $IC_{50}$ value of around 183 to 279 μM depending upon the experimental conditions, with no selectivity for COX-2. (Noreen et al. (1998) J. Nat. Prod. 61:1-7).

Green tea catechin, when supplemented into the diets of Sprague Dawley male rats, lowered the activity level of platelet $PLA_2$ and significantly reduced platelet cycloxygenase levels. (Yang et al. (1999) J. Nutr. Sci. Vitaminol. 45:337-346). Catechin and epicatechin reportedly weakly suppress cox-2 gene transcription in human colon cancer DLD-1 cells ($IC_{50}$=415.3 μM). (Mutoh et al. (2000) Jpn. J. Cancer Res. 91:686-691). The neuroprotective ability of (+)-catechin from red wine results from the antioxidant properties of catechin, rather than inhibitory effects on intracellular enzymes, such as cyclooxygenase, lipoxygenase, or nitric oxide synthase (Bastianetto et al. (2000) Br. J. Pharmacol. 131:711-720). Catechin derivatives purified from green and black tea, such as epigallocatechin-3-gallate (EGCG), epigallocatechin (EGC), epicatechin-3-gallate (ECG), and theaflavins showed inhibition of cycloxygenase and lipoxygenase dependent metabolism of AA in human colon mucosa and colon tumor tissues (Hong et al. (2001) Biochem. Pharmacol. 62:1175-1183) and induce cox-2 expression and $PGE_2$ production (Park et al. (2001) Biochem. Biophys. Res. Commun. 286: 721-725). Epiafzelechin isolated from the aerial parts of *Celastrus orbiculatus* exhibited dose-dependent inhibition of COX-1 activity with an $IC_{50}$ value of 15 μM and also demonstrated anti-inflammatory activity against carrageenin-induced mouse paw edema following oral administration at a dosage of 100 mg/kg. (Min et al. (1999) Planta Med. 65:460-462).

*Acacia* is a genus of leguminous trees and shrubs. The genus *Acacia* includes more than 1000 species belonging to the family of Leguminosae and the subfamily of Mimosoideae. Acacias are distributed worldwide in tropical and subtropical areas of Central and South America, Africa, parts of Asia, as well as, Australia, which has the largest number of endemic species. Acacias are very important economically, providing a source of tannins, gums, timber, fuel and fodder. Tannins, which are isolated primarily from bark, are used extensively for tanning hides and skins. Some *Acacia* barks are also used for flavoring local spirits. Some indigenous species like *A. sinuata* also yield saponins, which are any of various plant glucosides that form soapy lathers when mixed and agitated with water. Saponins are used in detergents, foaming agents and emulsifiers. The flowers of some *Acacia* species are fragrant and used to make perfume. The heartwood of many Acacias is used for making agricultural implements and also provides a source of firewood. *Acacia* gums find extensive use in medicine and confectionary and as sizing and finishing materials in the textile industry.

To date, approximately 330 compounds have been isolated from various *Acacia* species. Flavonoids are the major class of compounds isolated from *Acacias*. Approximately 180 different flavonoids have been identified, 111 of which are flavans. Terpenoids are second largest class of compounds isolated from species of the *Acacia* genus, with 48 compounds having been identified. Other classes of compounds isolated from *Acacia* include, alkaloids (28), amino acids/peptides (20), tannins (16), carbohydrates (15), oxygen heterocycles (15) and aliphatic compounds (10). (Buckingham, *The Combined Chemical Dictionary*, Chapman & Hall CRC, version 5:2, December 2001).

Phenolic compounds, particularly flavans are found in moderate to high concentrations in all *Acacia* species. (Abdulrazak et al. (2000) Journal of Animal Sciences. 13:935-940). Historically, most of the plants and extracts of the *Acacia* genus have been utilized as astringents to treat gastrointestinal disorders, diarrhea, indigestion and to stop bleeding. (Vautrin (1996) Universite Bourgogne (France) European abstract 58-01C: 177; Saleem et al. (1998) Hamdard Midicus. 41:63-67). The bark and pods of *Acacia arabica* Willd. contain large quantities of tannins and have been utilized as astringents and expectorants. (Nadkarni (1996) India Materia Medica, Bombay Popular Prakashan, pp. 9-17). Diarylpropanol derivatives, isolated from stem bark of *Acacia tortilis* from Somalia, have been reported to have smooth muscle relaxing effects. (Hagos et al. (1987) Planta Medica. 53:27-31, 1987). It has also been reported that terpenoid saponins isolated from *Acacia victoriae* have an inhibitory effect on dimethylbenz(a)anthracene-induced murine skin carcinogenesis (Hanausek et al. (2000) Proceedings American Association for Cancer Research Annual Meeting 41:663) and induce apotosis (Haridas et al. (2000) Proceedings American Association for Cancer Research Annual Meeting. 41:600). Plant extracts from *Acacia nilotica* have been reported to have spasmogenic, vasoconstrictor and antihypertensive activity (Amos et al. (1999) Phytotherapy Research 13:683-685; Gilani et al. (1999) Phytotherapy Research. 13:665-669), and antiplatelet aggregatory activity (Shah et al. (1997) General Pharmacology. 29:251-255). Anti-inflammatory activity has been reported for *A. nilotica*. It was speculated that flavonoids, polysaccharides and organic acids were potential active components. (Dafallah and Al-Mustafa (1996) American Journal of Chinese Medicine. 24:263-269). To date, the only reported 5-lipoxygenase inhibitor isolated from *Acacia* is a monoterpenoidal carboxamide. (Seikine et al. (1997) Chemical and Pharmaceutical Bulletin. 45:148-11).

The extract from the bark of *Acacia* has been patented in Japan for external use as a whitening agent (Abe, JP10025238), as a glucosyl transferase inhibitor for dental applications (Abe, JP07242555), as a protein synthesis inhibitor (Fukai, JP 07165598), as an active oxygen scavenging agent for external skin preparations (Honda, JP 07017847, Bindra U.S. Pat. No. 6,1266,950) and as a hyaluronidase inhibitor for oral consumption to prevent inflammation, pollinosis and cough (Ogura, JP 07010768).

To date, Applicant is unaware of any reports of a formulation combining Free-B-ring flavonoids and flavans for use in the prevention and treatment of neurodegradation, neuroinflammation and cumulative cognitive declines, disorders and diseases.

SUMMARY OF THE INVENTION

The present invention includes methods that are effective in simultaneously inhibiting both the cycloxygenase (COX) and lipoxygenase (LOX) enzymes. The method for the simultaneous dual inhibition of the COX and LOX enzymes is comprised of administering a composition comprising a mixture of Free-B-Ring flavonoids and flavans synthesized and/or isolated from a single plant or multiple plants to a host in need thereof. This composition of matter is referred to herein as Lasoperin™. The ratio of Free-B-Ring flavonoids to flavans in the composition of matter can be adjusted based on the indications and the specific requirements with respect to prevention and treatment of a specific disease or condition. Generally, the ratio of the Free-B-Ring flavonoids to flavans in the composition can be in the range of 99.9:0.1 of Free-B-Ring flavonoids:flavans to 0.1:99.9 Free-B-Ring flavonoids:flavans. In specific embodiments of the present invention, the ratio of Free-B-Ring flavonoids to flavans is selected from the group consisting of approximately 90:10, 80:20, 70:30, 60:40, 50:50, 40:60, 30:70, 20:80 and 10:90. In one embodiment of this invention, the ratio of Free-B-Ring flavonoids:flavans in the composition of matter is 80:20. In a preferred embodiment, the Free-B-Ring flavonoids are isolated from a plant or plants in the *Scutellaria* genus of plants and the flavans are isolated from a plant or plants in the *Acacia* genus of plants. The efficacy of this method was demonstrated with purified enzymes, in different cell lines, in multiple animal models and eventually in a human clinical study.

Specifically, the present includes methods for the prevention and treatment of COX and LOX mediated diseases and conditions related to neuronal and cognitive function, said method comprising administering to a host in need thereof an effective amount of a composition comprising a mixture of Free-B-Ring flavonoids and flavans synthesized and/or isolated from a single plant or multiple plants and a pharmaceutically acceptable carrier. The ratio of Free-B-Ring flavonoids to flavans in the composition can be in the range of 99.9:0.1 of Free-B-Ring flavonoids:flavans to 0.1:99.9 Free-B-Ring flavonoids:flavans. In specific embodiments of the present invention, the ratio of Free-B-Ring flavonoids to flavans can be selected from the group consisting of approximately 90:10, 80:20, 70:30, 60:40, 50:50, 40:60, 30:70, 20:80 and 10:90. In one embodiment of the invention, the ratio of Free-B-Ring flavonoids:flavans in the composition of matter is approximately 80:20. In a preferred embodiment, the Free-B-Ring flavonoids are isolated from a plant or plants in the *Scutellaria* genus of plants and flavans are isolated from a plant or plants in the *Acacia* genus of plants.

In another embodiment, the present includes a method for the prevention and treatment of general cognitive decline, age-related memory loss, neuroinflammatory and neurodegenerative disorders, said method comprising administering to a host in need thereof an effective amount of a composition comprising a mixture of Free-B-Ring flavonoids and flavans synthesized and/or isolated from a single plant or multiple plants together with a pharmaceutically acceptable carrier. The ratio of Free-B-Ring flavonoids to flavans can be in the range of 99.9:0.1 to 0.1:99.9 Free-B-Ring flavonoids:flavans. In specific embodiments of the present invention, the ratio of Free-B-Ring flavonoids to flavans is from the group consisting of approximately 90:10, 80:20, 70:30, 60:40, 50:50, 40:60, 30:70, 20:80 and 10:90. In one embodiment of the invention, the ratio of Free-B-Ring flavonoids:flavans in the composition of matter is approximately 80:20. In a preferred embodiment, the Free-B-ring flavonoids are isolated from a plant or plants in the *Scutellaria* genus of plants and flavans are isolated from a plant or plants in the *Acacia* genus of plants.

In another embodiment, the present invention includes a method for modulating the production of mRNA implicated in cognitive decline and other age-, neurodegenerative-, and neuroinflammatory-related conditions, said method comprising administering to a host in need thereof an effective amount of a composition comprising a mixture of Free-B-Ring flavonoids and flavans synthesized and/or isolated from a single plant or multiple plants and a pharmaceutically acceptable carrier. The ratio of Free-B-Ring flavonoids to flavans can be in the range of 99.9:0.1 to 0.1:99.9 Free-B-Ring flavonoids:flavans. In specific embodiments of the present invention, the ratio of Free-B-Ring flavonoids to flavans is selected from the group consisting of approximately 90:10, 80:20, 70:30, 60:40, 50:50, 40:60, 30:70, 20:80 and 10:90. In one embodiment of the invention, the ratio of Free-B-Ring flavonoids:flavans in the composition of matter is approximately 80:20. In one embodiment the Free-B-Ring flavonoids are isolated from a plant or plants in the *Scutellaria* genus of plants and flavans are isolated from a plant or plants in the *Acacia* genus of plants.

The present invention also includes a method for modulating the production of mRNA of transcription factors that control production of cytokine mRNA implicated in cognitive decline and other age-, neurodegenerative-, and neuroinflammatory-related conditions, said method comprising administering to a host in need thereof an effective amount of a composition comprising a mixture of Free-B-Ring flavonoids and flavans synthesized and/or isolated from a single plant or multiple plants and a pharmaceutically acceptable carrier. The ratio of Free-B-Ring flavonoids to flavans can be in the range of 99.9:0.1 to 0.1:99.9 Free-B-Ring flavonoids:flavans. In specific embodiments of the present invention, the ratio of Free-B-Ring flavonoids to flavans is selected from the group consisting of approximately 90:10, 80:20, 70:30, 60:40, 50:50, 40:60, 30:70, 20:80 and 10:90. In one embodiment of the invention, the ratio of Free-B-Ring flavonoids:flavans in the composition of matter is approximately 80:20. In a preferred embodiment the Free-B-Ring flavonoids are isolated from a plant or plants in the *Scutellaria* genus of plants and flavans are isolated from a plant or plants in the *Acacia* genus of plants.

In yet another embodiment, the present invention includes a method for modulating the production of mRNA transcription factors that controls production of cox-2, but not cox-1 mRNA implicated in cognitive decline and other age-, neurodegenerative-, and neuroinflammatory-related conditions, said method comprising administering to a host in need thereof an effective amount of a composition comprising a mixture of Free-B-Ring flavonoids and flavans synthesized and/or isolated from a single plant or multiple plants and a pharmaceutically acceptable carrier. The ratio of Free-B-Ring flavonoids to flavans can be in the range of 99.9:0.1 to 0.1:99.9 Free-B-ring flavonoids:flavans. In specific embodiments of the present invention, the ratio of Free-B-Ring flavonoids to flavans is selected from the group consisting of approximately 90:10, 80:20, 70:30, 60:40, 50:50, 40:60, 30:70, 20:80 and 10:90. In one embodiment of the invention, the ratio of Free-B-Ring flavonoids:flavans in the composition of matter is approximately 80:20. In a preferred embodiment the Free-B-Ring flavonoids are isolated from a plant or plants in the *Scutellaria* genus of plants and flavans are isolated from a plant or plants in the *Acacia* genus of plants.

While not limited by theory, it is believed that the composition of the instant invention acts by inhibiting pro-inflammatory cytokines via down-regulation of the nuclear factor kappa B (NFκB) transcription factor, which controls gene expression of interleukin-1 beta (IL-1β), tumor necrosis factor-alpha (TNFα), and interleukin-6 (IL-6). It is also believed that the composition inhibits the gene expression of another transcription factor, peroxisome proliferator activated receptor gamma (PPARγ), which helps control the gene expression of cyclooxygenase-2 (COX-2). Additionally, the composition of the instant invention inhibits the activity of COX-2 and 5-lipoxygenase (5-LO) thereby suppressing the conversion of AA to prostaglandins, thromboxanes, and leukotrienes, each of which exacerbate inflammation. The composition also possesses a strong antioxidant capacity which neutralizes reactive oxygen species (ROS), molecules that can lead to greater NFκB expression, and thus, greater pro-inflammatory gene expression of cytokines.

The Free-B-Ring flavonoids, also referred to herein as Free-B-Ring flavones and flavonols, that can be used in accordance with the following invention include compounds illustrated by the following general structure:

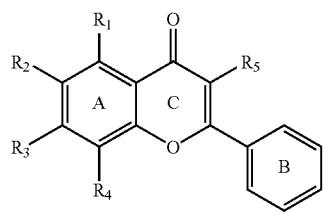

wherein $R_1$, $R_2$, $R_3$, $R_4$, and $R_5$ are independently selected from the group consisting of —H, —OH, —SH, OR, —SR, —NH$_2$, —NHR, —NR$_2$, —NR$_3{}^+$X$^-$, a carbon, oxygen, nitrogen or sulfur, glycoside of a single or a combination of multiple sugars including, but not limited to aldopentoses, methyl-aldopentose, aldohexoses, ketohexose and their chemical derivatives thereof;

wherein

R is an alkyl group having between 1-10 carbon atoms; and

X is selected from the group of pharmaceutically acceptable counter anions including, but not limited to hydroxyl, chloride, iodide, sulfate, phosphate, acetate, fluoride, carbonate, etc.

The Free-B-Ring flavonoids of this invention may be obtained by synthetic methods or extracted from the family of plants including, but not limited to Annonaceae, Asteraceae, Bignoniaceae, Combretaceae, Compositae, Euphorbiaceae, Labiatae, Lauranceae, Leguminosae, Moraceae, Pinaceae, Pteridaceae, Sinopteridaceae, Ulmaceae and Zingiberacea. The Free-B-Ring flavonoids can be extracted, concentrated, and purified from the following genus of high plants, including but not limited to *Desmos, Achyrocline, Oroxylum, Buchenavia, Anaphalis, Cotula, Gnaphalium, Helichrysum, Centaurea, Eupatorium, Baccharis, Sapium, Scutellaria, Molsa, Colebrookea, Stachys, Origanum, Ziziphora, Lindera, Actinodaphne, Acacia, Derris, Glycyrrhiza, Millettia, Pongamia, Tephrosia, Artocarpus, Ficus, Pityrogramma, Notholaena, Pinus, Ulmus* and *Alpinia*.

The flavans that can be used in accordance with the following invention include compounds illustrated by the following general structure: generally represented by the following general structure:

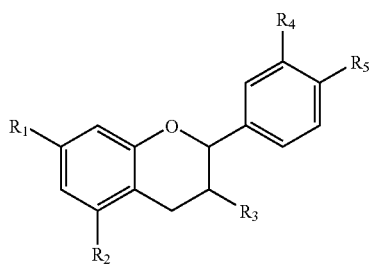

wherein $R_1$, $R_2$, $R_3$, $R_4$ and $R_5$ are independently selected from the group consisting of H, —OH, —SH, —OCH$_3$, —SCH$_3$, —OR, —SR, —NH$_2$, —NRH, —NR$_2$, —NR$_3{}^+$X$^-$, esters of substitution groups, including, but not limited to, gallate, acetate, cinnamoyl and hydroxyl-cinnamoyl esters, trihydroxybenzoyl esters and caffeoyl esters and their chemical derivatives thereof; carbon, oxygen, nitrogen or sulfur glycoside of a single or a combination of multiple sugars including, but not limited to, aldopentoses, methyl aldopentose, aldohexoses, ketohexose and their chemical derivatives thereof; dimer, trimer and other polymerized flavans;

wherein

R is an alkyl group having between 1-10 carbon atoms; and

X is selected from the group of pharmaceutically acceptable counter anions including, but not limited to hydroxyl, chloride, iodide, sulfate, phosphate, acetate, fluoride, carbonate, etc.

The flavans of this invention may be obtained from a plant or plants selected from the genus of *Acacia*. In a preferred embodiment, the plant is selected from the group consisting of *Acacia catechu, Acacia concinna, Acacia farnesiana, Acacia Senegal, Acacia speciosa, Acacia arabica, A. caesia, A. pennata, A. sinuata. A. mearnsii, A. picnantha, A. dealbata, A. auriculiformis, A. holoserecia* and *A. mangium*.

In one embodiment, the present invention includes a method for preventing and treating a number of COX and LOX mediated diseases and conditions related to neuronal and cognitive function, including, but not limited to general cognitive decline, age-related memory loss, neuroinflammatory and neurodegenerative disorders and other conditions relating to neuronal and cognitive function. In another embodiment, the present invention includes a method for modulating the production of mRNA implicated in cognitive decline and other age-, neurodegenerative-, and neuroinflammatory-related conditions.

The method of prevention and treatment according to this invention comprises administering to a host in need thereof a therapeutically effective amount of the formulated Free-B-Ring flavonoids and flavans isolated from a single source or multiple sources. The purity of the individual and/or a mixture of multiple Free-B-Ring flavonoids and flavans includes, but is not limited to 0.01% to 100%, depending on the methodology used to obtain the compound(s). In a preferred embodiment, doses of the mixture of Free-B-Ring flavonoids and flavans containing the same are an efficacious, nontoxic quantity generally selected from the range of 0.001% to 100% based on total weight of the formulation. Persons skilled in the art using routine clinical testing are able to determine optimum doses for the particular ailment being treated.

The present invention includes an evaluation of different compositions of Free-B-Ring flavonoids and flavans using enzymatic and in vivo models to optimize the formulation and obtain the desired physiological activity. The efficacy and safety of these formulations is demonstrated in human clinical studies. Thus, the present invention also includes therapeutic compositions comprising the therapeutic agents of the present invention. The compositions of this invention can be administered by any method known to one of ordinary skill in the art. The modes of administration include, but are not limited to, enteral (oral) administration, parenteral (intravenous, subcutaneous, and intramuscular) administration and topical application.

It is to be understood that both the foregoing general description and the following detailed description are exemplary and explanatory only and are not restrictive of the invention as claimed.

BRIEF DESCRIPTION OF THE DRAWINGS

FIG. 1A illustrates the results following pre-testing during weeks 1 and 2 (Baseline). FIG. 1B illustrates the results following week 5 (Session II) and FIG. 1C illustrates the results following week 11 (Session III).

FIG. 14 illustrates the effect of Lasoperin™ on the lipopolysaccharide (LPS)-induced level of cox-1, cox-2, il-1β, tnfα, il-6, nfκb and pparγ in peripheral blood monocytes (PBMC) from three subjects following exposure for four hours as described in Example 11.

DETAILED DESCRIPTION OF THE INVENTION

Figure 1A:
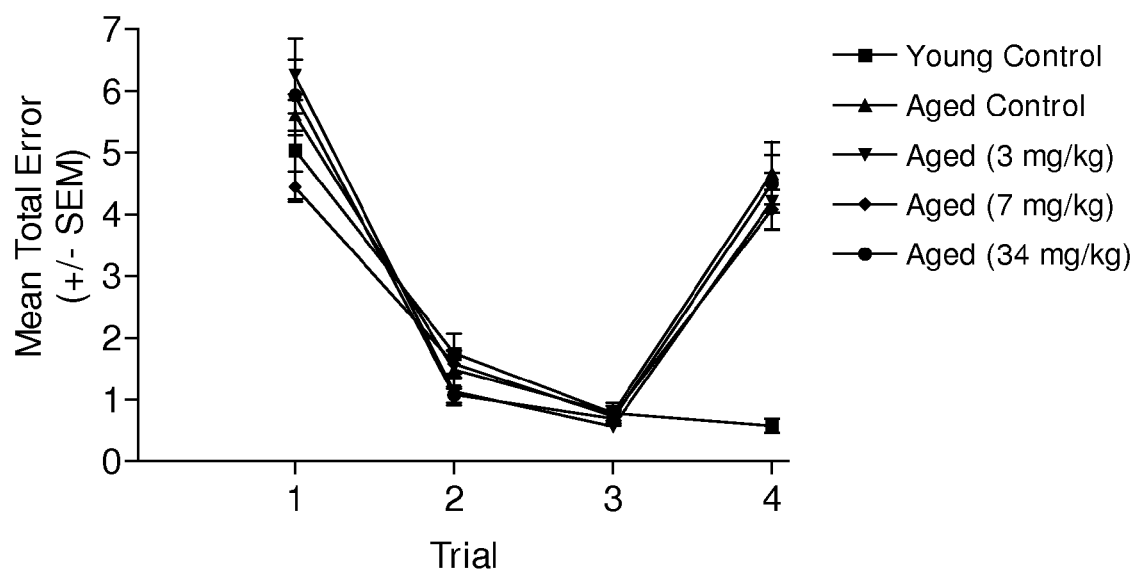
FIGS. 1A-1C depict graphically the effect of Lasoperin™ administered daily in a 13-week radial arm water maze (RAWM) test to Fisher 344 aged male rats fed a normal diet and a diet supplemented with 3, 7 or 34 mg/kg of Lasoperin™, respectively, as described in Example 2. The Lasoperin™ formulation (80:20) was prepared as described in Example 1 using two standardized extracts isolated from the bark of *Acacia catechu* and the roots of *Scutellaria baicalensis*. Young Fisher 344 male rats, maintained on a normal diet, served as a control for normal age-related changes in behavior. The data are presented as the mean total errors vs. trial number (four trials were performed on each test day).

The present invention includes methods that are effective in simultaneously inhibiting both the cycloxygenase (COX) and lipoxygenase (LOX) enzymes, for use in the prevention and treatment of diseases and conditions related to neuronal and cognitive function. The method for the simultaneous dual inhibition of the COX and LOX enzymes is comprised of administering a composition comprising a mixture of Free-B-Ring flavonoids and flavans synthesized and/or isolated from a single plant or multiple plants to a host in need thereof. This composition of matter is referred to herein as Lasoperin™. The ratio of Free-B-Ring flavonoids to flavans in the composition of matter can be adjusted based on the indications and the specific requirements with respect to prevention and treatment of a specific disease or condition.

Various terms are used herein to refer to aspects of the present invention. To aid in the clarification of the description of the components of this invention, the following definitions are provided.

Unless defined otherwise all technical and scientific terms used herein have the meaning commonly understood by one of ordinary skill in the art to which this invention belongs.

It is to be noted that as used herein the term "a" or "an" entity refers to one or more of that entity; for example, a flavonoid refers to one or more flavonoids. As such, the terms "a" or "an", "one or more" and "at least one" are used interchangeably herein.

"Free-B-ring Flavonoids" as used herein are a specific class of flavonoids, which have no substitute groups on the aromatic B-ring, as illustrated by the following general structure:

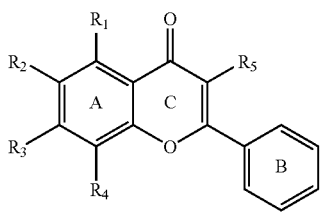

wherein
$R_1$, $R_2$, $R_3$, $R_4$, and $R_5$ are independently selected from the group consisting of —H, —OH, —SH, OR, —SR, —NH$_2$, —NHR, —NR$_2$, —NR$_3^+$X$^-$, a carbon, oxygen, nitrogen or sulfur, glycoside of a single or a combination of multiple sugars including, but not limited to aldopentoses, methyl-aldopentose, aldohexoses, ketohexose and their chemical derivatives thereof;
wherein
R is an alkyl group having between 1-10 carbon atoms; and
X is selected from the group of pharmaceutically acceptable counter anions including, but not limited to hydroxyl, chloride, iodide, sulfate, phosphate, acetate, fluoride, carbonate, etc.

"Flavans" as used herein refer to a specific class of flavonoids, which can be generally represented by the following general structure:

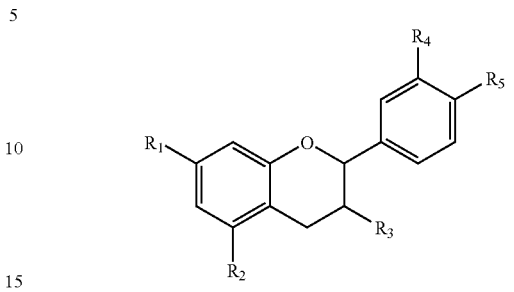

wherein
$R_1$, $R_2$, $R_3$, $R_4$ and $R_5$ are independently selected from the group consisting of H, —OH, —SH, —OCH$_3$, —SCH$_3$, —OR, —SR, —NH$_2$, —NRH, —NR$_2$, —NR$_3^+$X$^-$, esters of substitution groups, including, but not limited to, gallate, acetate, cinnamoyl and hydroxyl-cinnamoyl esters, trihydroxybenzoyl esters and caffeoyl esters and their chemical derivatives thereof; carbon, oxygen, nitrogen or sulfur glycoside of a single or a combination of multiple sugars including, but not limited to, aldopentoses, methyl aldopentose, aldohexoses, ketohexose and their chemical derivatives thereof; dimer, trimer and other polymerized flavans;
wherein
R is an alkyl group having between 1-10 carbon atoms; and
X is selected from the group of pharmaceutically acceptable counter anions including, but not limited to hydroxyl, chloride, iodide, sulfate, phosphate, acetate, fluoride, carbonate, etc.

"Therapeutic" as used herein, includes treatment and/or prophylaxis. When used, therapeutic refers to humans as well as other animals.

"Pharmaceutically or therapeutically effective dose or amount" refers to a dosage level sufficient to induce a desired biological result. That result may be the alleviation of the signs, symptoms or causes of a disease or any other alteration of a biological system that is desired. The precise dosage will vary according to a variety of factors, including but not limited to the age and size of the subject, the disease and the treatment being effected.

"Placebo" refers to the substitution of the pharmaceutically or therapeutically effective dose or amount dose sufficient to induce a desired biological that may alleviate the signs, symptoms or causes of a disease with a non-active substance.

A "host" or "patient" or "subject" is a living mammal, human or animal, for whom therapy is desired. The "host," "patient" or "subject" generally refers to the recipient of the therapy to be practiced according to the method of the invention.

As used herein a "pharmaceutically acceptable carrier" refers to any carrier, which does not interfere with effectiveness of the biological activity of the active ingredient and which is not toxic to the host to which it is administered. Examples of "pharmaceutically acceptable carriers" include, but are not limited to, any of the standard pharmaceutical carriers such as a saline solution, i.e. Ringer's solution, a buffered saline solution, water, a dextrose solution, serum albumin. and other excipients and preservatives for tableting and capsulating formulations.

"Gene expression" refers to the transcription of a gene to mRNA.

"Protein expression" refers to the translation of mRNA to a protein.

"RT-qPCR" as used herein refers to a method for reverse transcribing (RT) an mRNA molecule into a cDNA molecule and then quantitatively evaluating the level of gene expression using a polymerase chain reaction (PCR) coupled with a fluorescent reporter.

Note that throughout this application various citations are provided. Each of these citations is specifically incorporated herein by reference in its entirety.

The present invention includes methods that are effective in simultaneously inhibiting both the COX and LOX enzymes for use in the prevention and treatment of diseases and conditions related to neuronal and cognitive function. The method for the simultaneous dual inhibition of the COX and LOX enzymes is comprised of administering a composition comprised of a mixture of Free-B-Ring flavonoids and flavans synthesized and/or isolated from a single plant or multiple plants to a host in need thereof. This composition of matter which is referred to herein as Lasoperin™, is also distributed under the trade name of Univestin™, as described in U.S. patent application Ser. No. 10/427,746, filed Apr. 30, 2003, entitled "Formulation with Dual Cox-2 and 5-Lipoxygenase Inhibitory Activity," which is incorporated herein by reference in its entirety. The ratio of Free-B-Ring flavonoids to flavans can be in the range of 99.9:0.1 Free-B-Ring flavonoids:flavans to 0.1:99.9 Free-B-Ring flavonoids:flavans. In specific embodiments of the present invention, the ratio of Free-B-Ring flavonoids to flavans is selected from the group consisting of approximately 90:10, 80:20, 70:30, 60:40, 50:50, 40:60, 30:70, 20:80 and 10:90. In one embodiment of the invention, the ratio of Free-B-Ring flavonoids:flavans in the composition of matter is approximately 80:20.

The isolation and identification of Free-B-Ring flavonoids from the *Scutellaria* genus of plants is described in U.S. patent application Ser. No. 10/091,362, filed Mar. 1, 2002, entitled "Identification of Free-B-Ring Flavonoids as Potent Cox-2 Inhibitors," which is incorporated herein by reference in its entirety. The isolation identification of flavans from the *Acacia* genus of plants is described in U.S. patent application Ser. No. 10/104,477, filed Mar. 22, 2002, entitled "Isolation of a Dual Cox-2 and 5-Lipoxygenase Inhibitor from *Acacia*," which is incorporated herein by reference in its entirety.

The present invention includes methods that are effective in the prevention and treatment of age-, cognitive-, neurodegenerative- and neuroinflammatory-related diseases and conditions. The method for the prevention and treatment of these cognitive and neuronal diseases and conditions is comprised of administering to a host in need thereof a composition comprising a mixture of Free-B-Ring flavonoids and flavans synthesized and/or isolated from a single plant or multiple plants. The ratio of Free-B-Ring flavonoids to flavans in the composition can be in the range of 99.9:0.1 Free-B-Ring flavonoids:flavans to 0.1:99.9 of Free-B-Ring flavonoids:flavans. In specific embodiments of the present invention, the ratio of Free-B-Ring flavonoids to flavans is selected from the group consisting of approximately 90:10, 80:20, 70:30, 60:40, 50:50, 40:60, 30:70, 20:80 and 10:90. In one embodiment of the invention, the ratio of Free-B-Ring flavonoids:flavans in the composition of matter is approximately 80:20.

Further included in the present invention are methods for preventing and treating pro-inflammatory cytokine-mediated neuronal and cognitive diseases and conditions said method comprised of administering to a host in need thereof an effective amount of a composition comprising a mixture of Free-B-Ring flavonoids and flavans synthesized and/or isolated from a single plant or multiple plants together with a pharmaceutically acceptable carrier. The ratio of Free-B-Ring flavonoids to flavans in the composition can be in the range of 99.9:0.1 Free-B-Ring flavonoids:flavans to 0.1:99.9 of Free-B-Ring flavonoids:flavans. In specific embodiments of the present invention, the ratio of Free-B-Ring flavonoids to flavans is selected from the group consisting of approximately 90:10, 80:20, 70:30, 60:40, 50:50, 40:60, 30:70, 20:80 and 10:90. In one embodiment of the invention, the ratio of Free-B-Ring flavonoids:flavans in the composition of matter is approximately 80:20.

Also included in the present invention is a method for the reduction of TNFα and IL-1β, two key components in age-, cognitive-, neurodegenerative and neuroinflammatory-related diseases and conditions. The method for the reduction of TNFα and IL-1β is comprised of administering to a host in need thereof an effective amount of a composition comprising a mixture of Free-B-Ring flavonoids and flavans synthesized and/or isolated from a single plant or multiple plants together with a pharmaceutically acceptable carrier. The ratio of Free-B-Ring flavonoids to flavans in the composition can be in the range of 99.9:0.1 Free-B-ring flavonoids:flavans to 0.1:99.9 of Free-B-Ring flavonoids:flavans. In specific embodiments of the present invention, the ratio of Free-B-Ring flavonoids to flavans is selected from the group consisting of approximately 90:10, 80:20, 70:30, 60:40, 50:50, 40:60, 30:70, 20:80 and 10:90. In a preferred embodiment of the invention, the ratio of Free-B-Ring flavonoids:flavans in the composition of matter is approximately 80:20.

The present further includes a method for the prevention and treatment of diseases and conditions mediated by ROS, via the reduction of ROS. ROS are a pivotal product of oxidative stress and lipid metabolism and can be significantly elevated in age-, cognitive-, neurodegenerative- and neuroinflammatory-related diseases and conditions. The method for treating ROS-mediated diseases and conditions is comprised of administering to a host in need thereof an effective amount of a composition comprising a mixture of Free-B-Ring flavonoids and flavans synthesized and/or isolated from a single plant or multiple plants, together with a pharmaceutically acceptable carrier. The ratio of Free-B-Ring flavonoids to flavans in the composition can be in the range of 99.9:0.1 Free-B-Ring flavonoids:flavans to 0.1:99.9 of Free-B-Ring flavonoids:flavans. In specific embodiments of the present invention, the ratio of Free-B-Ring flavonoids to flavans is selected from the group consisting of approximately 90:10, 80:20, 70:30, 60:40, 50:50, 40:60, 30:70, 20:80 and 10:90. In one embodiment of the invention, the ratio of Free-B-Ring flavonoids:flavans in the composition of matter is approximately 80:20.

Finally, the present invention also includes a method for modulating the production of mRNA implicated in cognitive decline and other age-, neurodegenerative-, and neuroinflammatory-related conditions, including a method for modulating the production of mRNA of transcription factors that control the production of cytokine mRNA and a method for modulating the production of mRNA of the transcription factors that control the production of cox-2, but not cox-1 mRNA. The method for modulating the production of m-RNA implicated in cognitive decline and other age-, neurodegenerative-, and neuroinflammatory-related conditions is comprised of administering to a host in need thereof an effective amount of a composition comprising a mixture of Free-B-Ring flavonoids and flavans synthesized and/or isolated from a single plant or multiple plants together with a pharmaceutically acceptable carrier. The ratio of Free-B-Ring flavonoids to flavans can be in the range of 99:1 to 1:99 Free-B-Ring flavonoids:flavans. In specific embodiments of the present invention, the ratio of Free-B-Ring flavonoids to flavans is selected from the group consisting of approximately 90:10, 80:20, 70:30, 60:40, 50:50, 40:60, 30:70, 20:80 and 10:90. In one embodiment of the invention, the ratio of Free-B-Ring flavonoids:flavans in the composition of matter is approximately 80:20.

The Free-B-ring flavonoids that can be used in accordance with the following include compounds illustrated by the general structure set forth above. The Free-B-Ring flavonoids of this invention may be obtained by synthetic methods or may be isolated from the family of plants including, but not limited to Annonaceae, Asteraceae, Bignoniaceae, Combretaceae, Compositae, Euphorbiaceae, Labiatae, Lauranceae, Leguminosae, Moraceae, Pinaceae, Pteridaceae, Sinopteridaceae, Ulmaceae, and Zingiberaceae. The Free-B-Ring flavonoids can also be isolated from the following genera of high plants, including but not limited to *Desmos, Achyrocline, Oroxylum, Buchenavia, Anaphalis, Cotula, Gnaphalium, Helichrysum, Centaurea, Eupatorium, Baccharis, Sapium, Scutellaria, Molsa, Colebrookea, Stachys, Origanum, Ziziphora, Lindera, Actinodaphne, Acacia, Derris, Glycyrrhiza, Millettia, Pongamia, Tephrosia, Artocarpus, Ficus, Pityrogramma, Notholaena, Pinus, Ulmus*, and *Alpinia*.

The Free-B-Ring flavonoids can be found in different parts of plants, including but not limited to stems, stem barks, twigs, tubers, roots, root barks, young shoots, seeds, rhizomes, flowers and other reproductive organs, leaves and other aerial parts. Methods for the isolation and purification of Free-B-Ring flavonoids are described in U.S. application Ser. No. 10/091,362, filed Mar. 1, 2002, entitled "Identification of Free-B-ring Flavonoids as Potent COX-2 Inhibitors," and U.S. application Ser. No. 10/427,746, filed Apr. 30, 2003, entitled "Formulation with Dual Cox-2 and 5-Lipoxygenase Inhibitory Activity", each of which is incorporated herein by reference in its entirety.

The flavans that can be used in accordance with the method of this invention include compounds illustrated by the general structure set forth above. The flavans of this invention may be obtained by synthetic methods or may be isolated from a plant selected from the group including, but not limited to *Acacia catechu, A. concinna, A. farnesiana, A. Senegal, A. speciosa, A. arabica, A. caesia, A. pennata, A. sinuata. A. mearnsii, A. picnantha, A. dealbata, A. auriculiformis, A. holoserecia, A. mangium, Uncaria gambir, Uncaria tomentosa, Uncaria africana* and *Uncaria qabir*.

The flavans can be found in different parts of plants, including but not limited to stems, stem barks, trunks, trunk barks, twigs, tubers, roots, root barks, young shoots, seeds, rhizomes, flowers and other reproductive organs, leaves and other aerial parts. Methods for the isolation and purification of flavans are described in U.S. application Ser. No. 10/104,477, filed Mar. 22, 2002, entitled "Isolation of a Dual COX-2 and 5-Lipoxygenase Inhibitor from *Acacia*," which is incorporated herein by reference in its entirety.

In one specific embodiment of the invention, the Free-B-ring flavonoids are isolated from a plant or plants in the *Scutellaria* genus of plants and flavans are isolated from a plant or plants in the *Acacia* genus of plants.

The present invention implements a strategy that combines several in vivo cognitive tasks as well as in vitro biochemical, cellular and gene expression screens to identify active plant extracts that specifically inhibit COX and LOX enzymatic activity, decrease pro-inflammatory cytokines via down-regulation of key transcription factors that promote the production of the mRNA of said cytokines, and ROS production, maintain antioxidant properties pertaining to the prevention and treatment of neurodegradation, neuroinflammation, and cumulative cognitive declines, disorders, diseases and conditions resulting from the exposure to reactive oxygen species (ROS), inflammatory proteins, and eicosanoids. The extracts are further evaluated for their impact on mRNA gene expression. Free-B-Ring flavonoids and flavans were tested for their ability in prevent age-related cognitive decline when administered orally as an added component to food.

Example 1 sets forth a general method for the preparation of Lasoperin™, using two standardized extracts isolated from *Acacia* and *Scutellaria*, respectively, together with one or more excipient(s). With reference to Table 1, this specific batch of Lasoperin™ contained 86% total active ingredients, including 75.7% Free-B-Ring flavonoids and 10.3% flavans. One or more excipient(s) can optionally be added to the composition of matter. The amount of excipient added can be adjusted based on the actual active content of each ingredient desired.

Figure 1B:
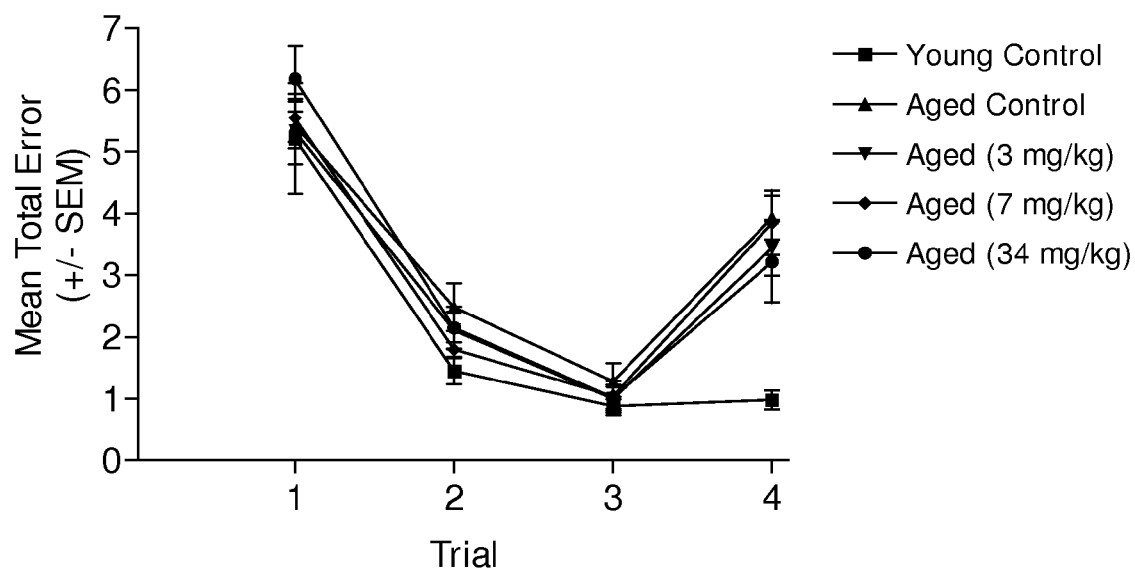
Figure 1C:
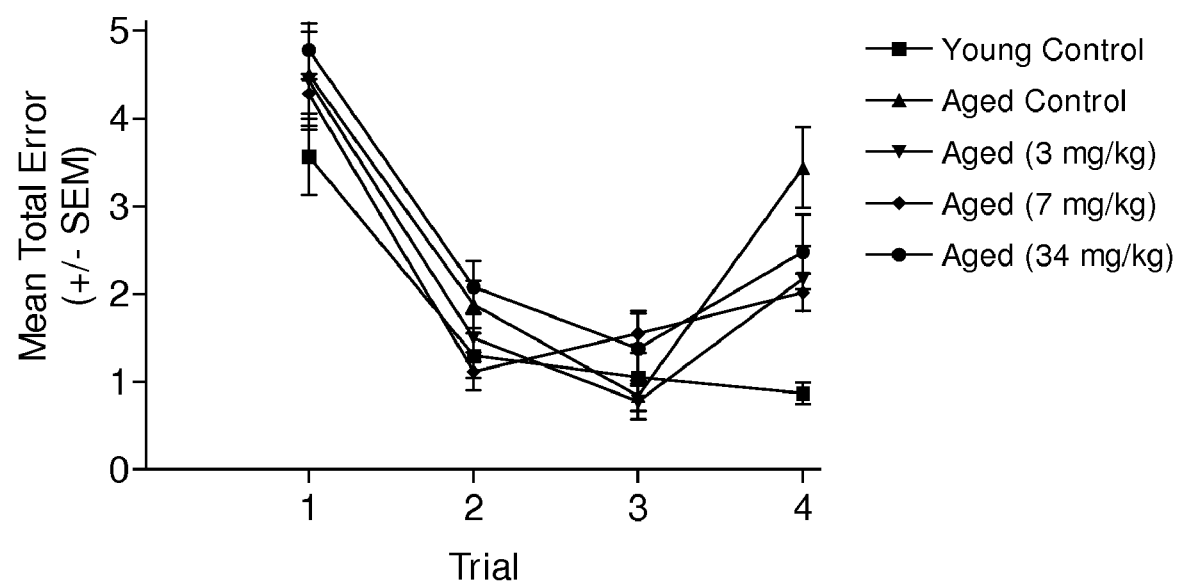

In order to evaluate the effects of Lasoperin™ on cognitive function two specific behavioral tests, the radial arm water maze (RAWM) and the contextual fear conditioning (CFC) test, which assess hippocampal-dependent working memory were carried out using an animal model. Example 2 illustrates the effect of Lasoperin™ on hippocampal-dependant cognitive function as measured by the radial arm water maze (RAWM) test. The results are set forth in FIGS. 1A-1C, which depict graphically the effect of Lasoperin™ administered daily in a 13-week radial arm water maze (RAWM) test to Fisher 344 aged male rats fed a diet supplemented with 3, 7 or 34 mg/kg Lasoperin™, respectively. Young Fisher 344 male rats, maintained on a normal diet, served as a control for normal age-related changes in behavior. The data are presented as the mean total errors vs. trial number (four trials were performed on each test day). FIG. 1A illustrates the results following pre-testing during weeks 1 and 2 (baseline). FIG. 1B illustrates the results following week 5 (Session II) and FIG. 1C illustrates the results following week 11 (Session III). The data depicted in FIGS. 1A-C demonstrate that Lasoperin™ (7 and 34 mg/kg dose groups) prevents age-related memory impairment.

Figure 2:
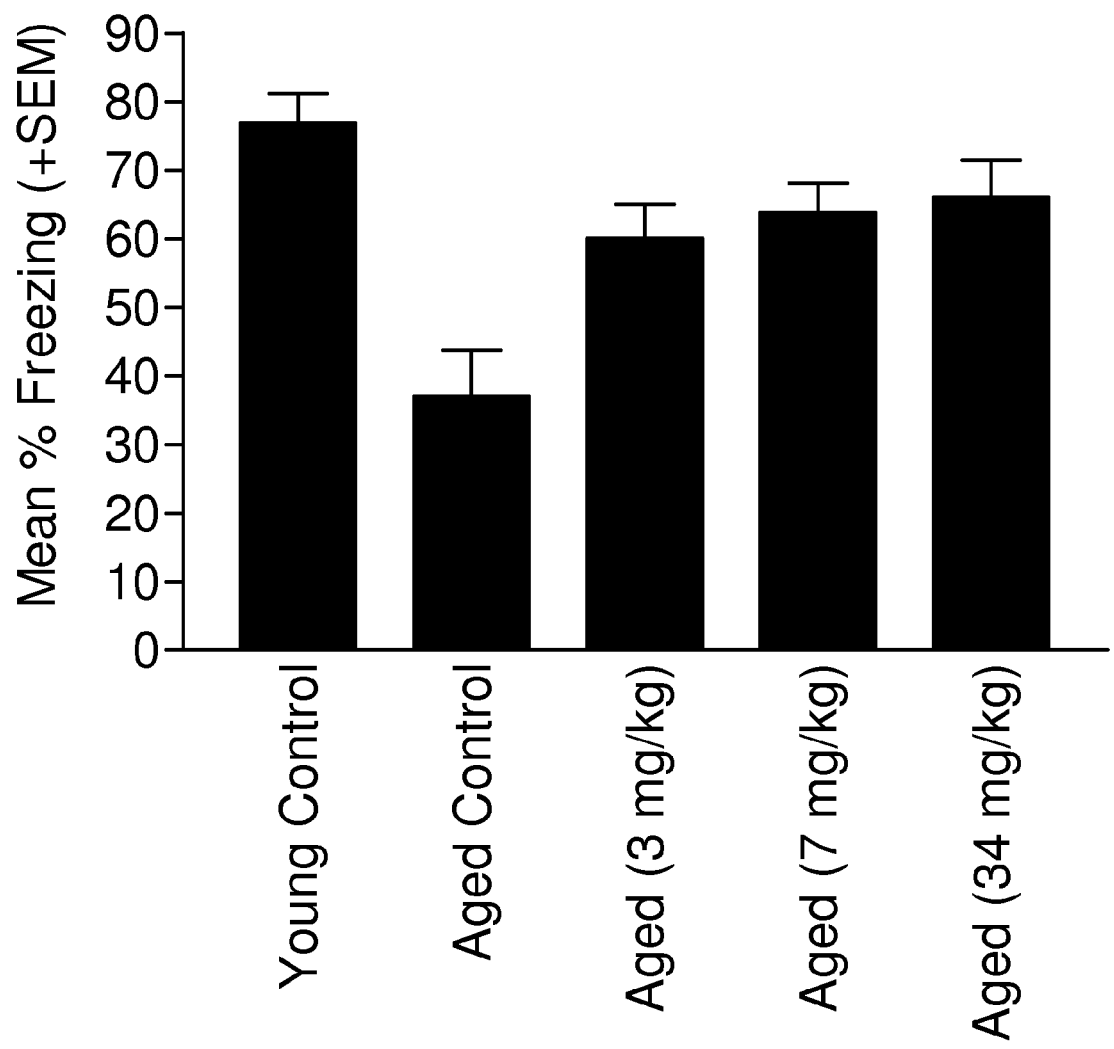
FIG. 2 illustrates the effect of Lasoperin™ administered daily for 12 weeks prior to contextual fear conditioning (CFC) testing in Fisher 344 aged male rats fed a normal diet or a diet supplemented with 3, 7 or 34 mg/kg Lasoperin™, as described in Example 3. The Lasoperin™ formulation (80:20) was prepared as described in Example 1 using two standardized extracts isolated from the bark of *Acacia catechu* and the roots of *Scutellaria baicalensis*. Young Fisher 344 male rats, maintained on a normal diet, served as a control for normal age-related changes in behavior. The data are presented as mean percent freezing vs. dose group.

Because the RAWM contains a motor function component, it is possible that an improvement in this task could be experienced if the administered formulation alleviated joint pain and discomfort. To control for this, the CFC test was also carried out as this test does not require the animal to move and therefore confirms the cognitive aspect of both tasks (nociceptive shock threshold was used to test for analgesic properties of the formulation in evaluating the CFC results). Example 3 illustrates the effect of Lasoperin™ on hippocampal-dependent cognitive function as measured by the contextual fear conditioning (CFC) test. Sixty Fisher 344 male rats were used in this study as described in Example 2. The results are set forth in FIG. 2, which illustrates the effect of Lasoperin™ administered daily for 12 weeks prior to contextual fear conditioning testing in 344 aged male rats fed a diet supplemented with 3, 7 or 34 mg/kg Lasoperin™. Young Fisher 344 male rats, maintained on a normal diet, served as a control for normal age-related changes in behavior. The data are presented as mean percent freezing vs. dose group. FIG. 2 demonstrates that Lasoperin™ (7 and 34 mg/kg dose groups) ameliorated age-related impairments.

Examples 4 and 5 illustrate the effect of Lasoperin™ administered daily at 300 mg/day over a 4 week period to 40 individuals in a randomized, placebo-controlled, double-blind clinical trial on cognitive function. The results were compared to 46 individuals who were treated with a placebo. Measurement of cognitive performance was obtained using a series of web-based Cognitive Care tests which assess Psychomotor speed, Working Memory Speed (executive decision making, quickness & flexibility) and Immediate Memory (verbal & spatial memory processing). Before the study began, participants were required to practice the tests on two consecutive days to establish baseline performance. The data analysis compares baseline performance to performance post-treatment.

Psychomotor speed or physical reflexes is a simple reaction time test that requires the person to respond by pressing a key as quickly as possible after a figure appears on the computer screen.

Working Memory Speed presents a word and picture simultaneously and requires the person to decide if they are the same or different. A reversal cue is also presented randomly and requires the person to respond opposite of the correct response, so that a response to a correct pair would be no and visa versa. This task requires suppression or "inhibition of a learned response" and then a reversal ("task shifting") of the response contingency. The speed of switching from one task or one response mode to another is often equated with mental flexibility and higher-order cognitive processing, as well as superior decision-making.

Immediate Memory is similar to the classic Sternberg task in which a string of stimulus "target" items to be remembered are followed by a "probe" item. The subject must determine if the probe item was a member of the previous target list. List length can be varied to provide an estimate of the short-term memory capacity of the individual. Both letters and spatial position are examined in this task.

Figure 3:
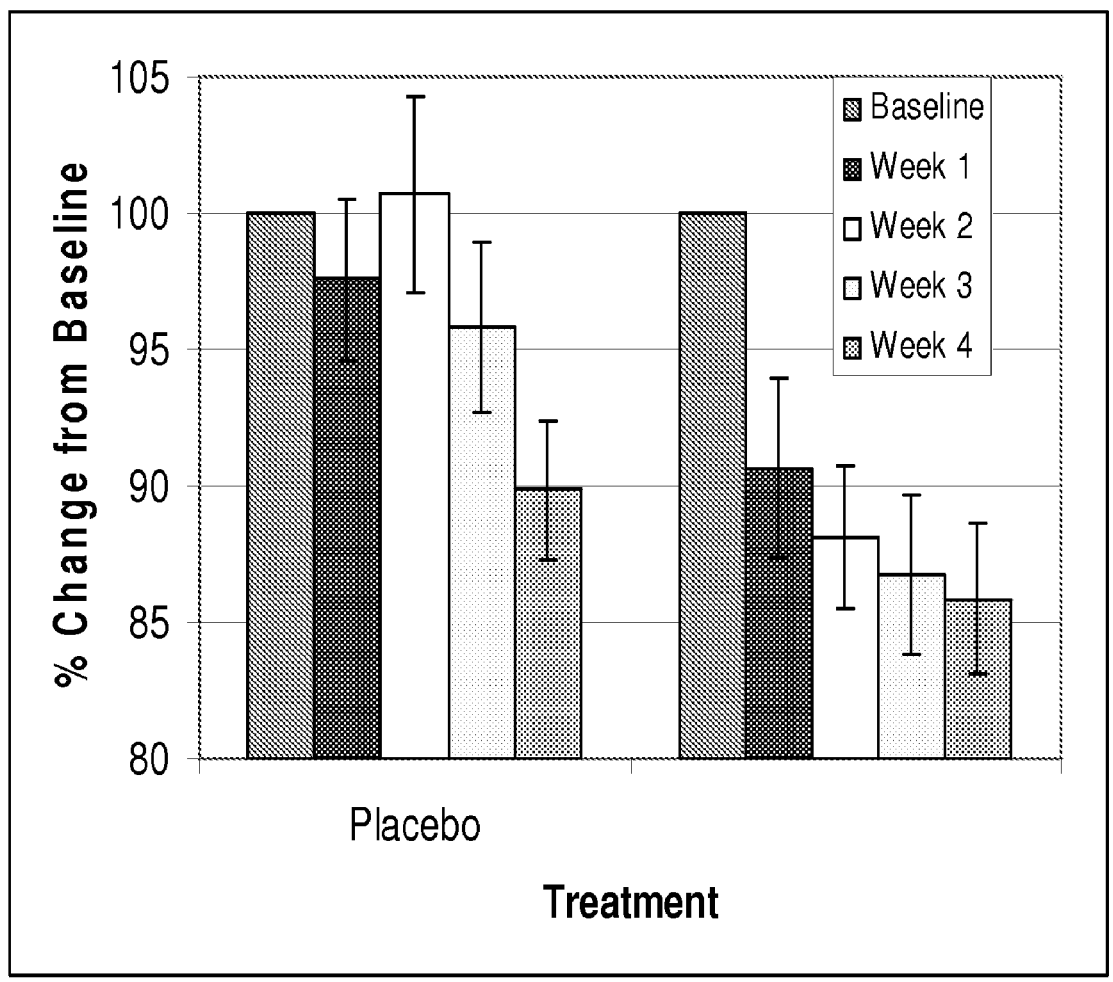
FIG. 3 depicts graphically the effect of Lasoperin™ on complex choice reaction time as described in Example 4. The Lasoperin™ was administered daily to 40 individuals in a 4 week clinical trial. The results are compared to a group of 46 individuals that were given a placebo over the same time period. The Lasoperin™ formulation (80:20) was prepared as described in Example 1 using two standardized extracts isolated from the bark of *Acacia catechu* and the roots of *Scutellaria baicalensis*. The data is presented as percent change from baseline. This figure demonstrates that Lasoperin™ (300 mg/d) increased speed of processing for subjects presented with complex choices and information.
Figure 4:
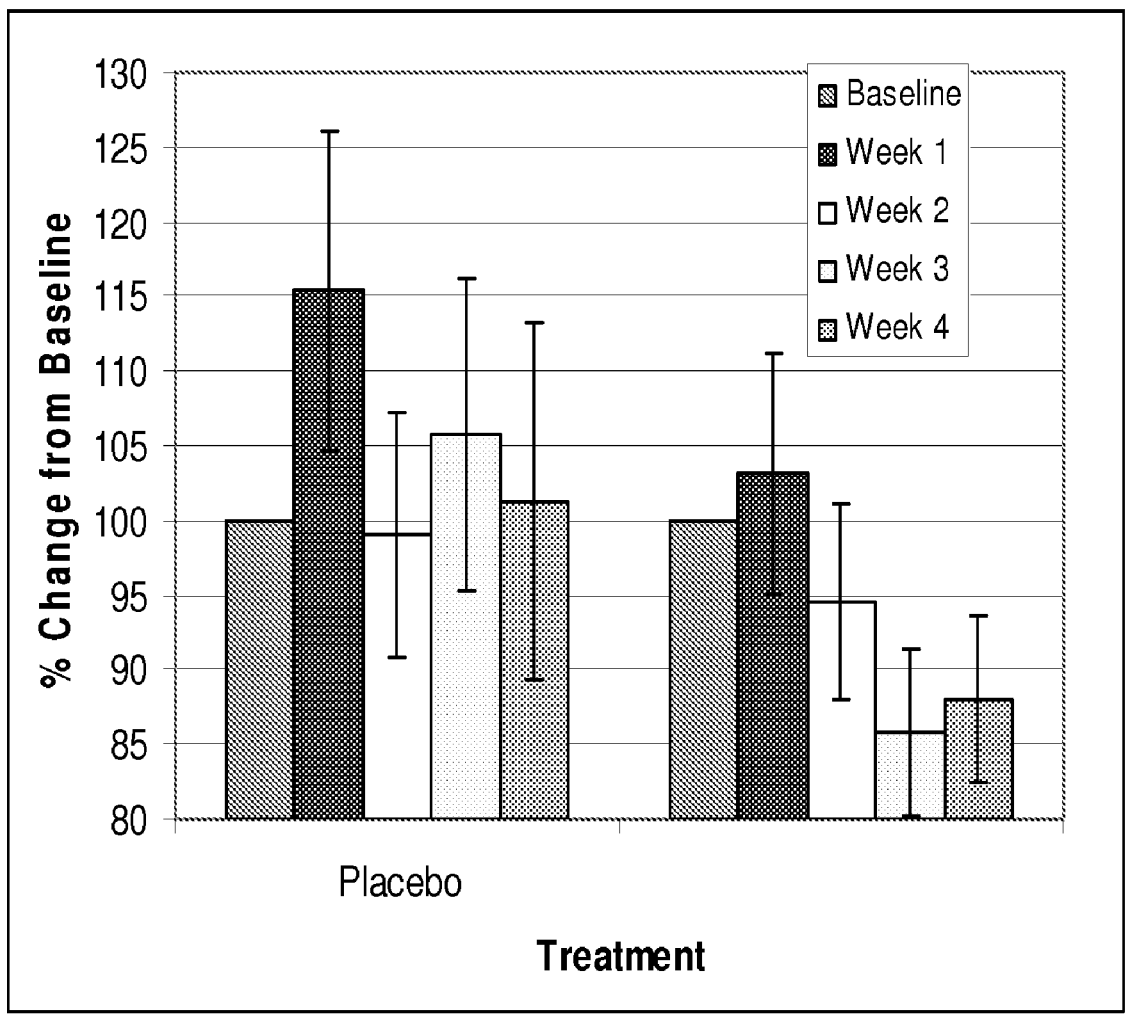
FIG. 4 depicts graphically the effect of Lasoperin™ on reaction time standard deviation (RTSD) as described in Example 5. The Lasoperin™ was administered daily to 40 individuals in a 4 week clinical trial. The results are compared to a group of 46 individuals that were given a placebo over the same time period. The Lasoperin™ formulation (80:20) was prepared as described in Example 1 using two standardized extracts isolated from the bark of *Acacia catechu* and the roots of *Scutellaria baicalensis*. The data is presented as percent change from baseline. This figure demonstrates that Lasoperin™ (300 mg/d) increased the intra-trial reaction time standard deviation, that is the ability to stay focused and attentive improved during demanding cognitive tasks.

The results are set forth in FIG. 3, which depicts graphically the effect of Lasoperin™ on complex choice reaction time and FIG. 4, which depicts graphically the effect of Lasoperin™ on reaction time standard deviation (RTSD). Reaction time standard deviation represents the intra-trial variance. FIGS. 3 and 4 demonstrate that Lasoperin™ increases the speed of processing in subjects presented with complex choices and information.

Figure 5:
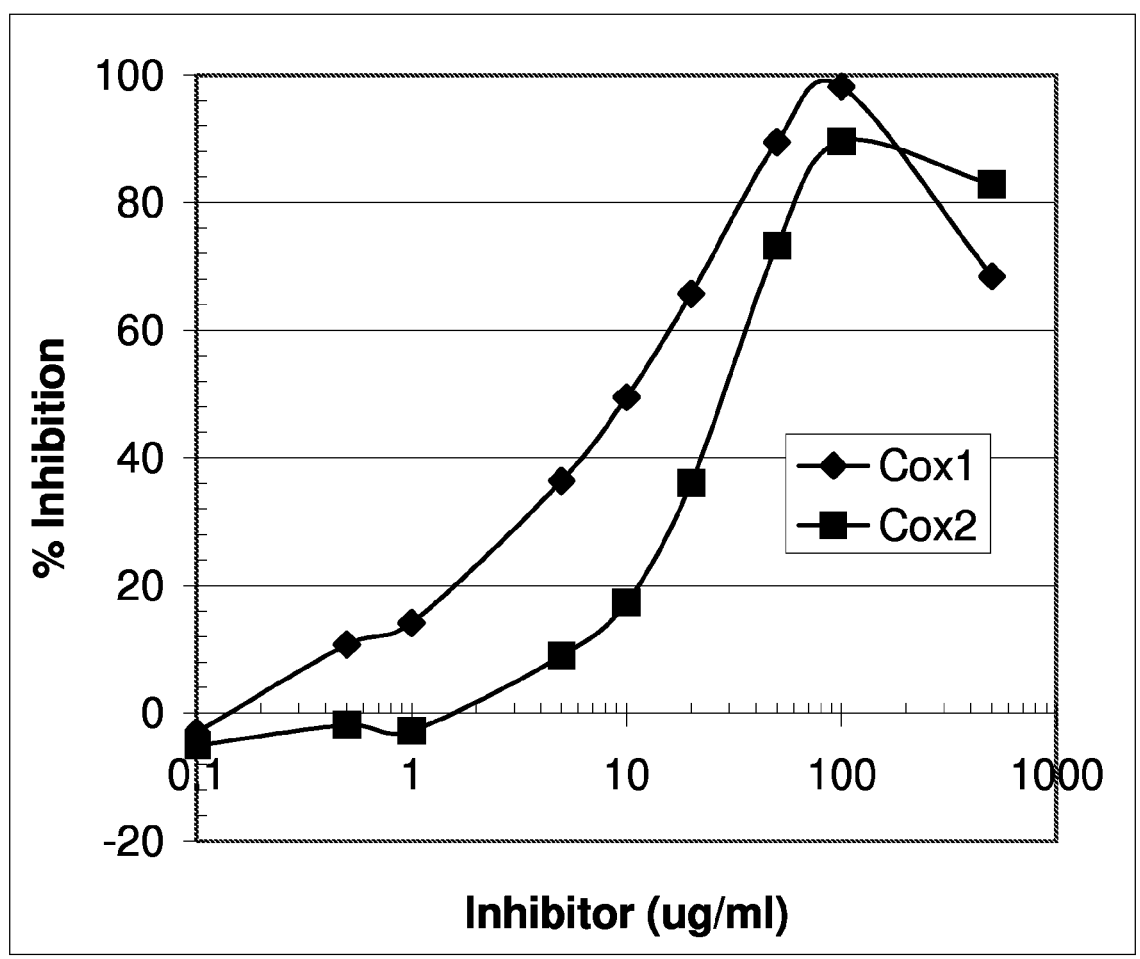
FIG. 5 depicts graphically the inhibition of COX-1 and COX-2 by Lasoperin™. The Lasoperin™ formulation (50:50) was prepared as described in Example 1 using two standardized extracts isolated from the bark of *Acacia catechu* and the roots of *Scutellaria baicalensis*. Lasoperin™ was examined for its inhibition of the peroxidase activity of recombinant ovine COX-1 (♦) and ovine COX-2 (■). The data is presented as percent inhibition vs. inhibitor concentration (µg/mL). The $IC_{50}$ for COX-1 was 0.38 µg/mL/unit of enzyme, while the $IC_{50}$ for COX-2 was 0.84 µg/mL/unit.

Example 6 describes a COX inhibition assay performed using Lasoperin™. The biochemical assay, used to measure inhibition of COX, relies on the protein's peroxidase activity in the presence of heme and arachidonic acid. The dose response and $IC_{50}$ results for Lasoperin™ are set forth in FIG. 5. The $IC_{50}$ for COX-1 was 0.38 µg/mL/unit of enzyme, while the $IC_{50}$ for COX-2 was 0.84 µg/mL/unit.

Figure 6:
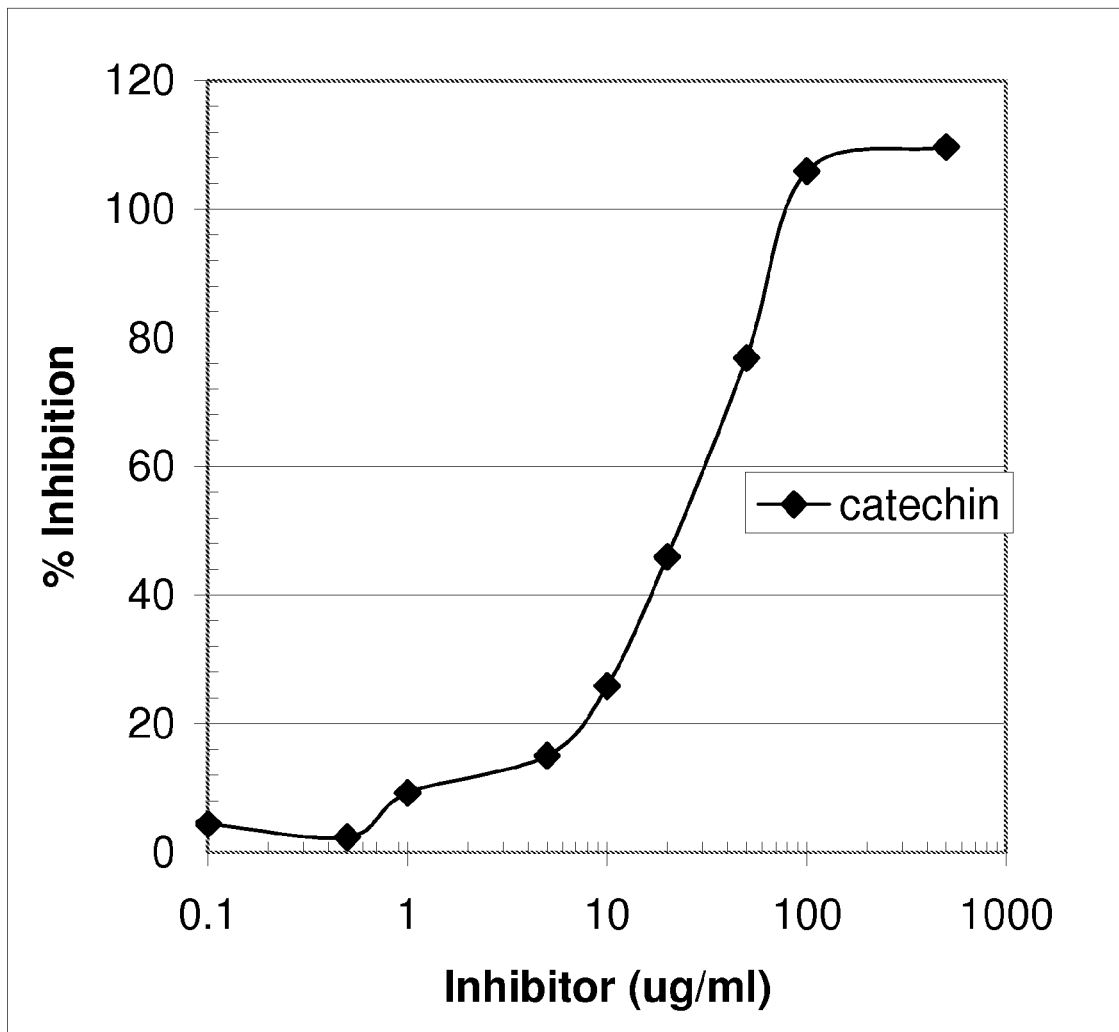
FIG. 6 depicts graphically a profile of the inhibition of 5-LO by the purified flavan catechin isolated from *A. catechu*. The compound was examined for its inhibition of recombinant potato 5-lipoxygenase activity (♦). The data is presented as percent inhibition of assays without inhibitor vs. inhibitor concentration (µg/mL). The $IC_{50}$ for 5-LO was 1.38 µg/mL/unit of enzyme.

Example 7 describes a LOX inhibition assay using the flavan catechin isolated from *A. catechu*. The inhibition of LOX activity was assessed using a lipoxygenase screening assay in vitro. The results of this assay are set forth in FIG. 6. The $IC_{50}$ for 5-LO inhibition by catechin was determined to be 1.38 µg/mL/unit of enzyme.

Figure 7:
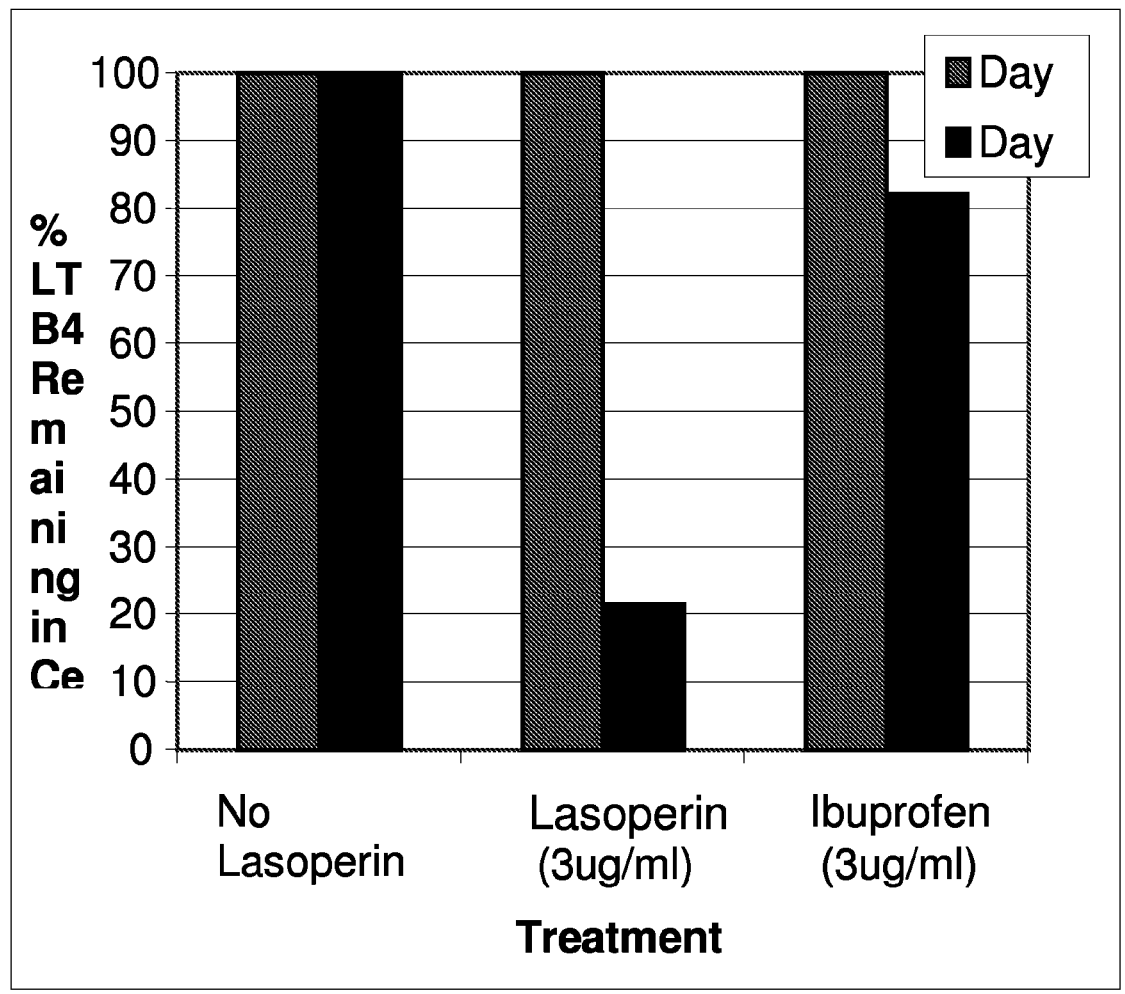
FIG. 7 compares the $LTB_4$ levels as determined by ELISA that remain in HT-29 cells after treatment with 3 µg/mL Lasoperin™ in non-induced cells to treatment with 3 µg/mL ibuprofen as described in Example 8. The Lasoperin™ formulation (80:20) was prepared as described in Example 1 using two standardized extracts isolated from the bark of *Acacia catechu* and the roots of *Scutellaria baicalensis*.

Example 8 describes cell assays performed that targeted inhibition of compounds in the breakdown of arachidonic acid in the LOX pathway, namely LTB4. The results are set forth in FIG. 7. With reference to FIG. 7 it can be seen that Lasoperin™ inhibited the generation of 80% of the newly synthesized $LTB_4$ in HT-29 cells. Ibuprofen showed only a 20% reduction in the amount of $LTB_4$ over the same time period.

Figure 8:
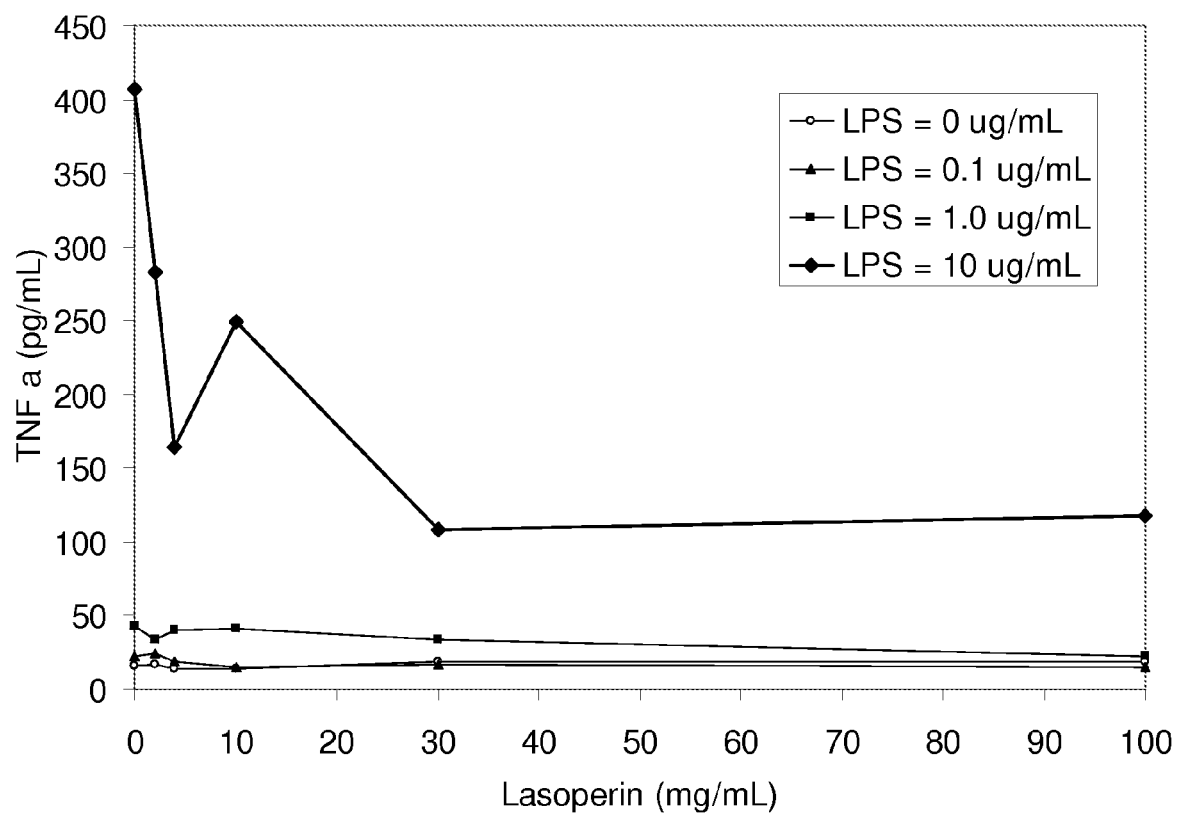
FIG. 8 illustrates graphically the effect of a mixture of Free-B-Ring flavonoids and flavans (80:20) on the lipopolysaccharide (LPS)-induced level of TNFα in peripheral blood monocytes (PBMC) following exposure to the lipopolysaccharide in conjunction with different concentrations of the Free-B-Ring flavonoid and flavan mixture for one hour. The level of TNFα is expressed in pg/mL.
Figure 9:
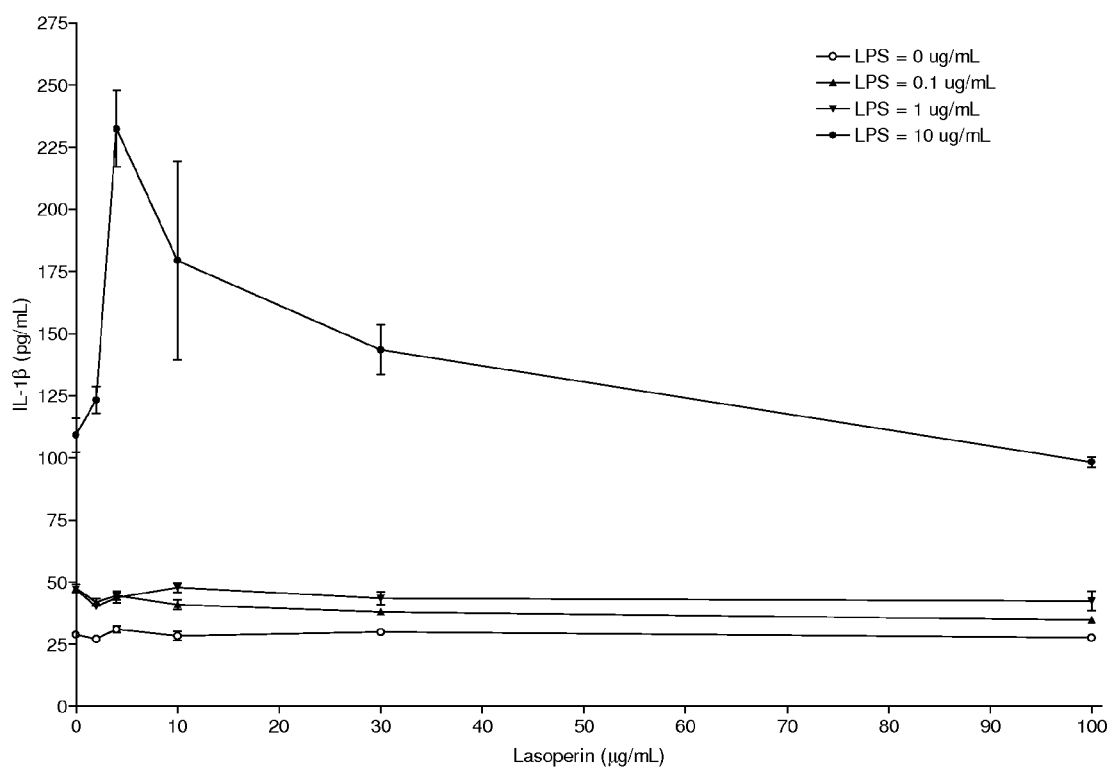
FIG. 9 depicts the effect of a mixture of Free-B-Ring flavonoids and flavans (80:20) on the lipopolysaccharide (LPS)-induced level of IL-11 in peripheal blood monocytes (PBMC) following exposure to the lipopolysaccharide in conjunction with different concentrations of the Free-B-Ring flavonoid and flavan mixture for four hours. The level of IL-1β is expressed in pg/mL.
Figure 10:
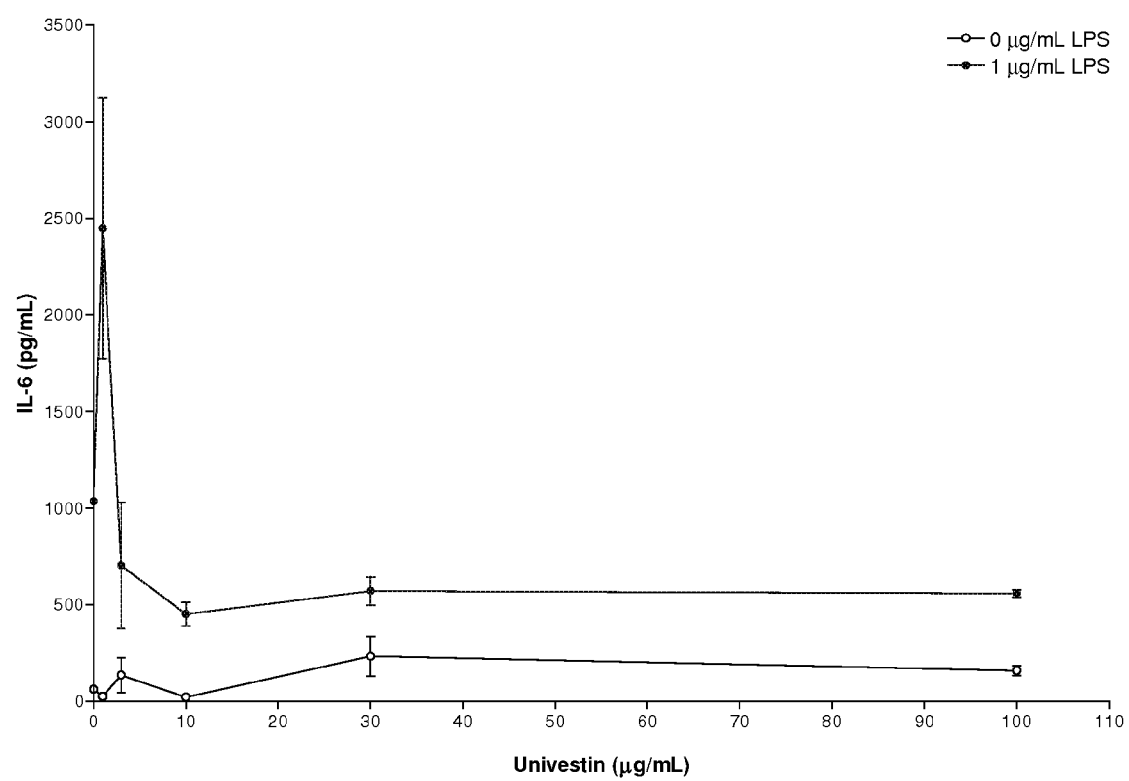
FIG. 10 illustrates graphically the effect of a mixture of Free-B-Ring flavonoids and flavans (80:20) on the lipopolysaccharide (LPS)-induced level of IL-6 in peripheal blood monocytes (PBMC) following exposure to the lipopolysaccharide in conjunction with different concentrations of the Free-B-Ring flavonoid and flavan mixture for four hours. The level of IL-6 is expressed in pg/mL. The standard deviation is shown for each data point.

Example 9 describes the measurement of the effect of Lasoperin™ on LPS-induced levels of TNFα, IL-1β, and IL-6 in Peripheral Blood Monocytes. The results are set forth in FIGS. 8-10. With reference to FIG. 8, it can be seen that the extract decreased TNFα secreted into the cell culture supernatant substantially over a wide range of concentrations from 2 to 100 µg/mL. With reference to these figures it can be seen that a concentration of 10 µg/mL of LPS showed the greatest level of TNFα and IL-1β induction following co-incubation with Lasoperin™ for one and four hours respectively. The extract decreased TNFα and IL-1β excreted in the cell culture supernatant substantially over a wide range of concentrations from 2 to 100 µg/mL (see FIGS. 8 and 9). Since TNFα, IL-1β, and IL-6 are elevated during inflammation and aging-related disorders, by decreasing these pro-inflammatory cytokines and transcription factors in primed inflammatory cells Lasoperin™ can have significant impact with respect to these disorders.

Figure 11:
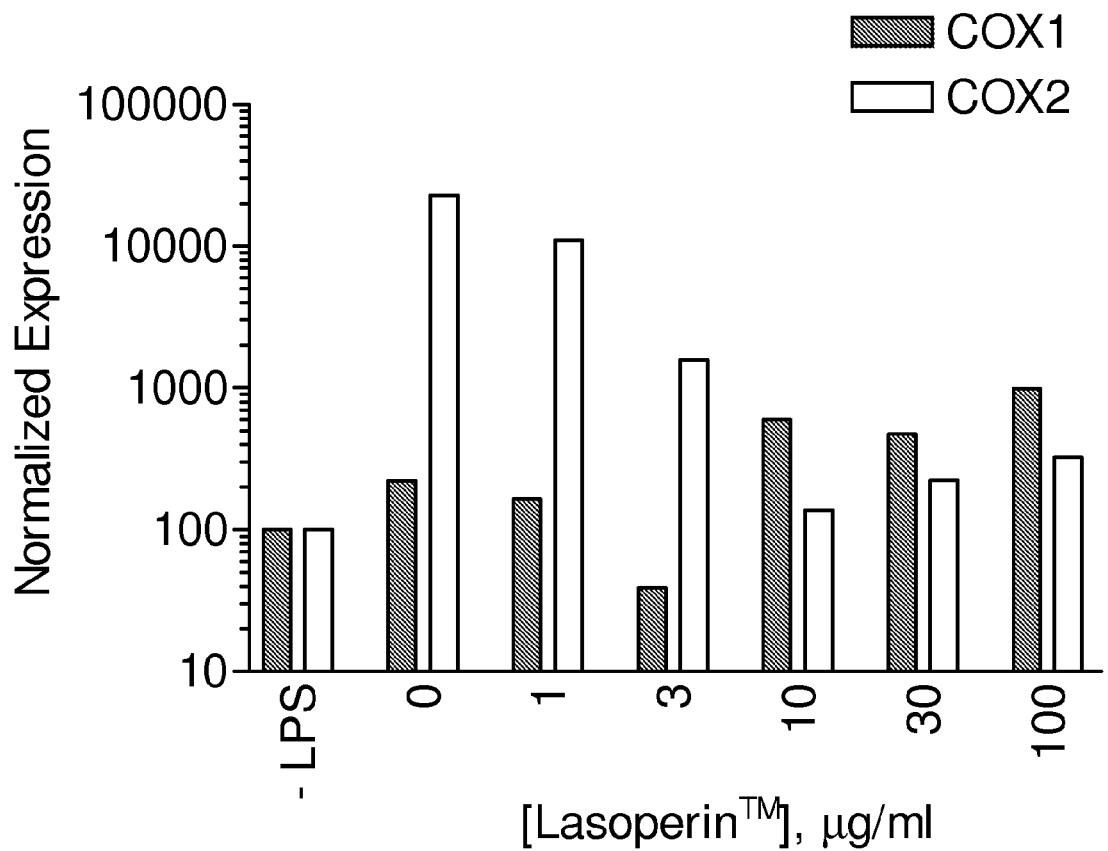
FIG. 11 compares the effect of various concentrations of Lasoperin™ on cox-1 and cox-2 gene expression. The expression levels are standardized to 18S rRNA expression levels (internal control) and then normalized to the no-treatment, no-LPS condition. This Figure demonstrates a decrease in cox-2, but not cox-1 gene expression following LPS-stimulation and exposure to Lasoperin™.
Figure 12:
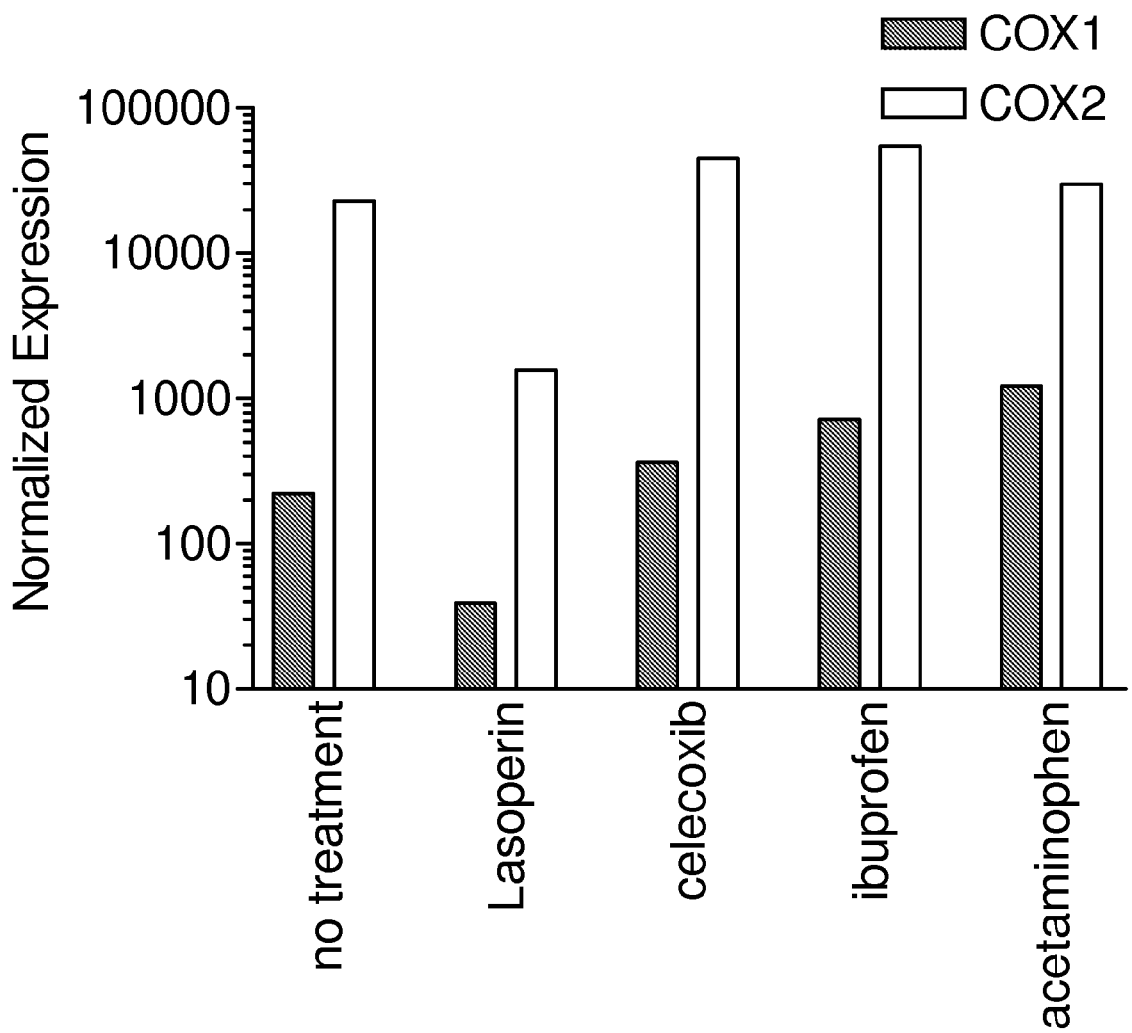
FIG. 12 compares the effect of 3 µg/mL Lasoperin™ on cox-1 and cox-2 gene expression with the equivalent concentration of other NSAIDs. The expression levels are standardized to 18S rRNA expression levels (internal control) and then normalized to the no-treatment, no-LPS condition.
Figure 13A:
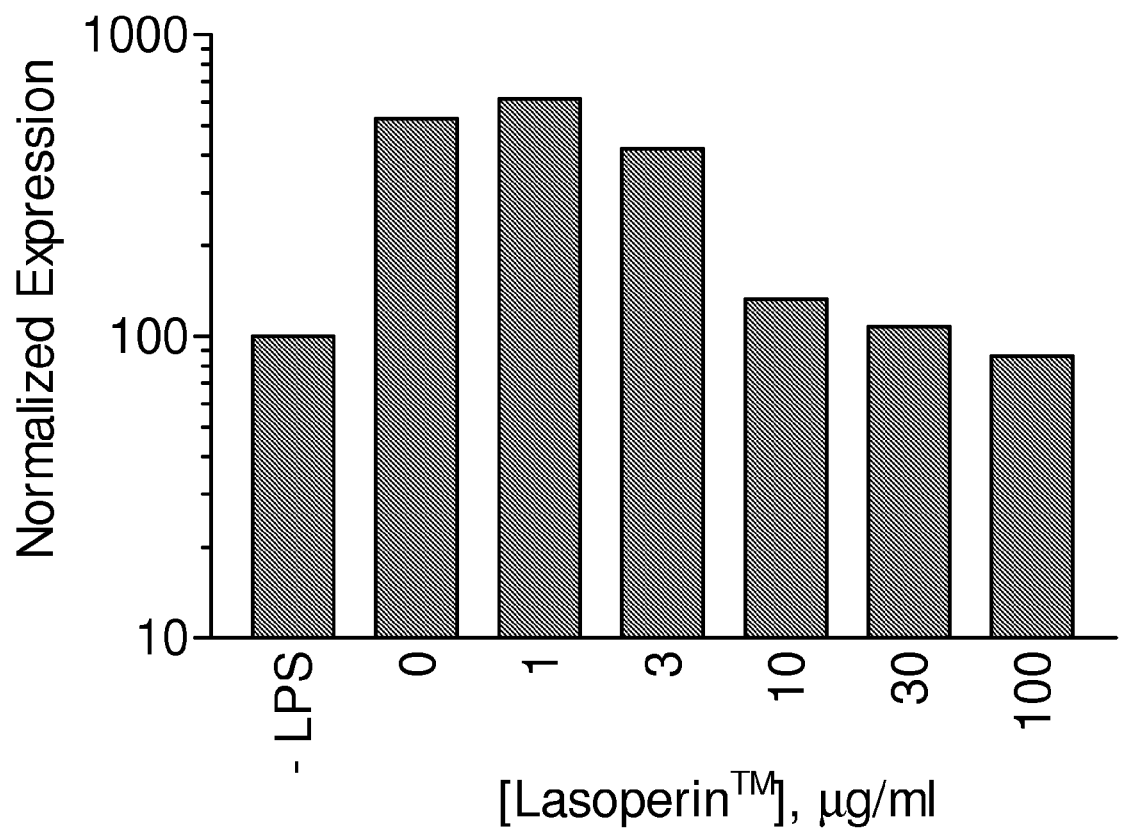
FIGS. 13A and 13B illustrate the effect of various concentrations of Lasoperin™ on tnfα-1 (FIG. 13A) and il-1β (FIG. 13B) gene expression. The expression levels are standardized to 18S rRNA expression levels (internal control) and then normalized to the no-treatment, no-LPS condition. These figures demonstrate a decrease in tnfa-1 and il-1β gene expression following LPS-stimulation and exposure to Lasoperin™.
Figure 13B:
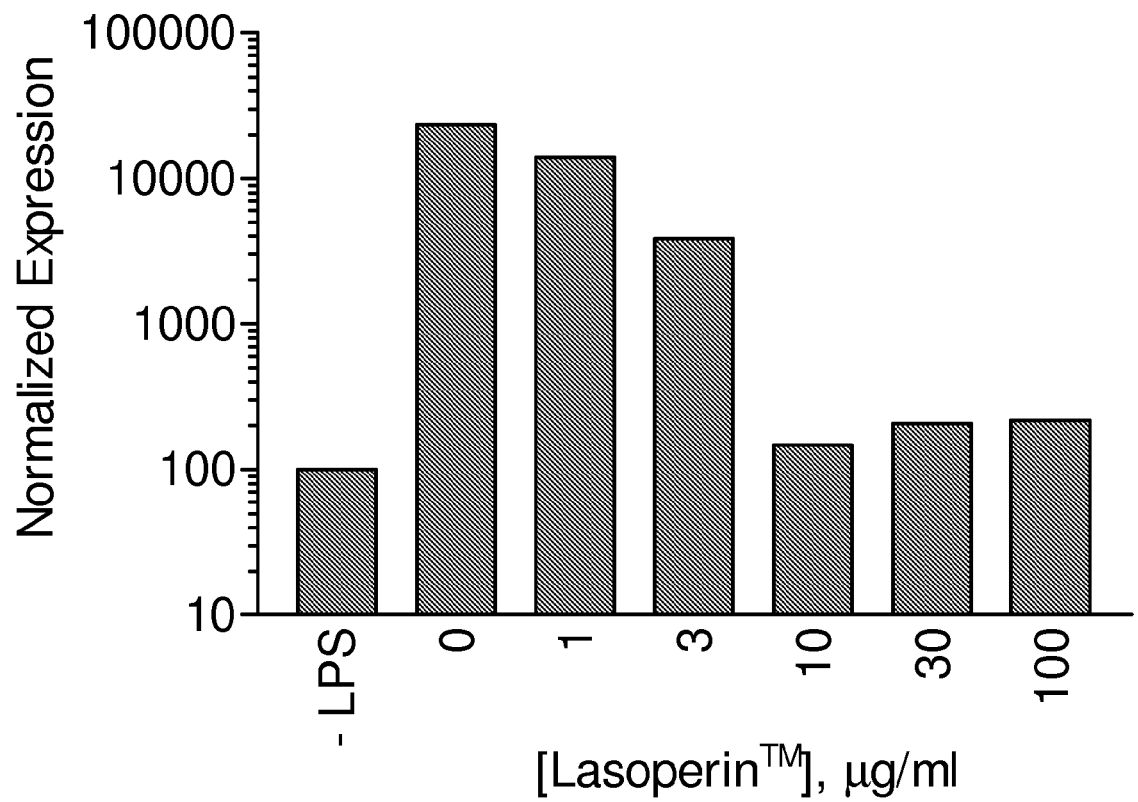

Example 10 describes an experiment performed to determine the differential inhibition of the cox-2 gene by Lasoperin™ versus other NSAIDS. Gene expression data was obtained for the inhibition of cox-1 and cox-2 mRNA production in a semi-quantitative RT-qPCR assay. The results are set forth in FIGS. 11-13. With reference to FIG. 11, it can be seen that Lasoperin™ inhibited cox-2 mRNA production without effecting cox-1 gene expression. In addition, when compared with other cox-2 inhibitor drugs, Lasoperin™ was able to decrease LPS-stimulated increases in cox-1 and cox-2 gene expression. Importantly, celecoxib and ibuprofen both increased cox-2 gene expression (FIG. 12). Finally, with reference to FIGS. 13A and B it can be seen that treatment with Lasoperin™ resulted in a decrease in the production of both tnfα-1 and il-1 αβ.

Example 11 describes an experiment performed to determine the effect of Lasoperin™ on the LPS-induced level of cox-1, cox-2, il-1β, tnfα, il-6, nfκb and pparγ in peripheral blood monocytes (PBMC) from three subjects following exposure for four hours as described in Example 11. The results are set forth in FIG. 14. With reference to FIG. 14, it can be seen that the Lasoperin™ extract decreased gene expression for all mRNA species significantly.

Figure 15:
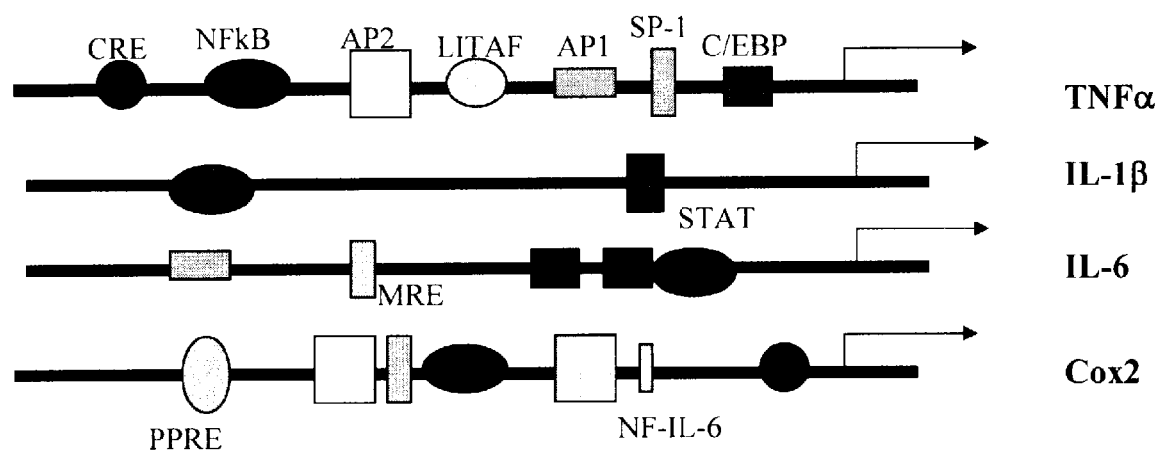
FIG. 15 illustrates the promoters for tnfα, il-1β, il-6 and cox-2 affected by down-regulation of nfκb and pparγ gene expression reduction.

Example 12 describes the down-regulation of promoter elements of inflammatory genes by Lasoperin™. These promoter elements are shown in FIG. 15.

Example 13 describes a method used to determine the effectiveness of Lasoperin™ as an antioxidant as measured by the Oxygen Radical Absorption Capacity (ORAC) test. The ORAC analysis, which utilizes fluorescein as a fluorescent probe, provides a measure of the capacity of antioxidants to scavenge for peroxyl radicals, which are one of the most common reactive oxygen species found in the body. The results are set forth in Table 2 which illustrates that relative to concentrates of several well-known food-based antioxidants. Lasoperin™ has a high ORAC score. In fact, the ORAC of Lasoperin™ is comparable to the antioxidant Vitamin C and thus should effectively decrease ROS levels in the body.

Examples 14 and 15 describe two methods used to determine the amount of Free-B-Ring flavonoids and flavans in the standardized extract. The results are set forth in FIGS. 16 and 17.

The following examples are provided for illustrative purposes only and are not intended to limit the scope of the invention.

EXAMPLES

Example 1

Preparation of Lasoperin™ from Extracts Isolated from *Acacia* and *Scutellaria*

Lasoperin™ was formulated using two standardized extracts isolated from *Acacia* and *Scutellaria*, respectively, together with one or more excipient(s). The *Acacia* extract used contained >60% total flavans, as catechin and epicatechin, and the *Scutellaria* extract contained >70% Free-B-

Ring flavonoids, which was primarily baicalin. The *Scutellaria* extract contained other minor amounts of Free-B-Ring flavonoids as set forth in Table 1. One or more excipient(s) were added to the composition of matter. The ratio of flavans and Free-B-Ring flavonoids can be adjusted based on the indications and the specific requirements with respect to inhibition of COX-2 vs. 5-LO and potency requirements of the product. The amount of the excipient(s) can be adjusted based on the actual active content of each ingredient. A blending table for each individual batch of product must be generated based on the product specification and quality control (QC) results. Additional amounts of active ingredients in the range of 2-5% are recommended to meet the product specification.

Table 1 illustrates a blending table generated for one batch of Lasoperin™ (lot # G1702-COX-2). Briefly, *Scutellaria baicalensis* root extract (38.5 kg) (lot # RM052302-01) having a Free-B-Ring flavonoid content of 82.2% (baicalin); *Acacia catechu* bark extract (6.9 kg) (lot # RM052902-01) with a total flavan content of 80.4% and the excipient Candex (5.0 kg) were combined to provide a Lasoperin™ formulation (50.4 kg) having a blending ratio of 85:15. Table 1 provides the quantification of the active Free-B-Ring flavonoids and flavans of this specific batch of Lasoperin™ (lot # G1702-COX-2), determined using the methods described in U.S. application Ser. No. 10/427,746, filed Apr. 30, 2003, entitled "Formulation With Dual Cox-2 And 5-Lipoxygenase Inhibitory Activity," which is incorporated herein by reference in its entirety.

TABLE 1

Free-B-Ring Flavonoid and Flavan content of a Lasoperin ™ Formulation

| Active Components | % Content |
|---|---|
| Flavonoids | |
| Baicalin | 62.5% |
| Minor flavonoids | |
| wogonin-7-glucuronide | 6.7% |
| oroxylin A 7-glucuronide | 2.0% |
| baicalein | 1.5% |
| wogonin | 1.1% |
| Chrysin-7-glucuronide | 0.8% |
| 5-methyl-wogonin-7-glucuronide | 0.5% |
| scutellarin | 0.3% |
| norwogonin | 0.3% |
| Chrysin | <0.2% |
| oroxylin A | <0.2% |
| Total Free-B-ring Flavonoids | 75.7% |
| Flavans | |
| catechin | 9.9% |
| epicatechin | 0.4% |
| Total Flavans | 10.3% |
| Total Active Ingredients | 86% |

With reference to Table 1, this specific batch of Lasoperin™ is comprised of 86% total active ingredients, including 75.7% Free-B-Ring flavonoids and 10.3% flavans. Two different dosage levels of final product in capsule form were produced from this batch of Lasoperin™ (50.0 kg): 125 mg per dose (60 capsules) and 250 mg per dose (60 capsules). Using the same approach, two additional batches of Lasoperin™ were prepared having a blending ratio of 50:50 and 20:80, respectively.

Example 2

Effect of Lasoperin™ on Hippocampal-Dependent Cognitive Function (RAWM)

A Lasoperin™ formulation (80:20) was prepared as described in Example 1. (See also Example 14 of U.S. patent application Ser. No. 10/427,746, filed Apr. 30, 2003, entitled "Formulation With Dual COX-2 And 5-Lipoxygenase Inhibitory Activity," which is incorporated herein by reference in its entirety) by combining a standardized Free-B-Ring flavonoid extract isolated from *Scutellaria baicalensis* roots and a standardized flavan extract isolated from *Acacia catechu* bark with a blending ratio of 80:20. To investigate the effect of Lasoperin™ on hippocampal-dependent cognitive function, the performance of sixty Fisher 344 male rats (ages listed below) was evaluated using a radial arm testing maze (RAWM). This test measures changes in learning and memory over the course of treatment. Baseline measurements were determined prior to starting the experimental diet and the test was performed again at 5 and 11 weeks subsequent to initiation of the experimental diet. The No Delay condition demonstrates the animal's ability to perform the task and acts as a control for differences in the ability to perform the task (e.g., locomotion, vision, motivation, etc.). The Delay condition introduces a 4 hour delay between trials 3 and 4, making the task more difficult. It is under the Delay condition that the age-related memory impairments are demonstrated.

Animals. Male Fischer 344 rats (National Institute on Aging contract colony; Harlan Sprague Dawley, Indianapolis, Ind.) (6 mo of age, n=12 and 17 mo of age, n=48) were housed in pairs, maintained in environmentally controlled chambers on a 12 hour light/dark cycle at 21±1° C. and provided food and water ad libitum. Young and aged control animals were provided with a NIH-31 (TD 00365; Harlan Teklab, Madison, Wis.) rodent diet. The test groups received a NIH-31 rodent diet supplemented with Lasoperin™ (3, 7 or 34 mg/kg). The control diet and the experimental formulation were prepared by Harlan Teklab and provided in extruded pellet form to the animals. The rats were microchipped to ensure proper identification during all aspects of the study. Due to the large number of animals, the experiment was split into two cohorts of 30 rats, which each group containing 6 animals. To obtain a baseline the animals were assessed in the RAWM prior to being placed on the experimental diet. Upon completion of the initial RAWM test, the aged rats were assigned to one of four groups (Aged Control, 3, 7, and 34 mg/kg Lasoperin™) in a counter-balanced manner, such that each group was equivocal in RAWM performance. Animal weight and food intake were monitored weekly to determine general health and the ingestion of food. No differences in these indexes were observed between groups.

Radial arm water maze (RAWM). The RAWM consisted of 12 arms (15 cm wide×43 cm long) emanating from a circular choice area (60 cm diameter) in a 1.5 m tank of water. An escape platform (10 cm×13 cm) was situated at the end of one of the arms, 2 cm below the surface of the water. Rats were pre-trained in the maze for five days. Pre-training consisted of shaping the animals to find the goal arm by initially blocking entry into the non-goal arms and gradually increasing the number of available arms until all 12 were open. The rats were then trained for two blocks of five days each. The entire training process required three weeks. The start arm for each trial was determined in a pseudo-random manner from the 11 available arms. A given arm was used only once per day so that there were four different start arms each day. To avoid place and position preferences, the start and goal arms were different for each animal within a group on a given day, but equivalent across groups. Four trials were administered per day (180 second (s) maximum) with a 30 s inter-trial interval. If a rat did not find the escape platform within 180 s, it was gently guided to the correct arm. The number of arms entered prior to entering the arm containing the escape platform (Errors) was recorded. A 3 hour delay was introduced between trials three and four for days six through ten. During the delay, the rats were placed back into their home cage. The results are set forth in FIGS. 1A-C. Data are presented as the mean for each trial versus trial number.

With reference to FIGS. 1A-C, in all sessions there was a significant decrease in Total Errors as the trials progressed, indicating that the rats could learn the task. In the No Delay task, there were no age- or drug-related differences in performance. In the Delay task, there was a significant age effect for all three delay sessions (Baseline, Session II, and Session III; see FIGS. 1A, B and C, respectively). The aged animals performed significantly worse in trial 4 than did the young controls. There was no effect due to the drug during the Baseline (FIG. 1A) and the Session II (FIG. 1B) Delay tests. There was, however, a significant effect due to the drug in the Session III delay test (FIG. 1C). The 7 and 34 mg/kg groups had significantly fewer errors than did the Aged Controls. They were not significantly different from the Young Controls, suggesting that Lasoperin™ prevented the age-related memory impairment. The analyses are 2-way ANOVA with repeated measures.

Example 3

Effect of Lasoperin™ on Hippocampal-Dependent Cognitive Function (CFC)

Sixty Fisher 344 male rats were used in this study as described in Example 2.

Contextual fear conditioning (CFC). One week after completing the RAWM testing, the rats were placed in a box (30.5 cm×24.1 cm×21 cm, Med Associates, St. Albans, Vt.) with a grid floor (4.8 mm diameter rods, spaced 1.6 cm apart) connected to a constant current shocker (Med Associates). Prior to placing each rat in the box, the box was cleaned with 3% acetic acid, which functioned as a specific odorant for the original context. Two consecutive training blocks were administered. Each training block was 180 seconds (s) long with a 30 s, 85-dB white noise conditioned stimulus (CS) and a 2 s, 0.5 mA footshock (US). The CS and US co-terminated at the end of the training block. All rats reacted to the footshock by jumping. The rats remained in the training box for 30 s following the second training block. Retention was tested 2 days after training by first placing the animals in the same apparatus, using 3% acetic acid as an odorant, in which training was performed for 5 minutes (min), without the CS or US. Two to three hours later, the rats were placed in a the same chamber except that the grid floor was covered with a piece of black Formica and the cage was cleaned with 3% ammonium hydroxide (Novel Context) for 6 min, during which the CS was administered for the final 3 min. Freezing was quantified manually every 10 s by an experimenter blind to the treatment groups of the rats. At 10 s intervals the experimenter assessed whether the rat was freezing or not. Percent freezing was calculated as: number of intervals during which the rat was assessed as freezing/by the total number of intervals ×100. The results are set forth in FIG. 2.

Freezing in the Training Context: In this analysis, there was a statistically significant decrease in freezing in the aged controls compared to the young controls (see FIG. 2). The 7 and 34 mg/kg doses of Lasoperin™ ameliorated this age-related impairment. There was a non-statistically significant trend for the 3 mg/kg dose to ameliorate the age-related impairment. None of the Lasoperin™-treated rats were significantly different from the young controls.

Freezing to the noise conditioned stimulus (CS) measures non-hippocampal dependent memory. With respect to this measurement, there were no statistically significant differences in freezing between any of the groups (data not shown).

Freezing to the novel context is a control measure to determine baseline freezing. To obtain this measurement, the amount of freezing that occurs during the training context and the CS are compared to the baseline freezing to determine if learning occurred. There were no statistically significant differences in freezing between any of the groups (data not shown).

Nociceptive Threshold. The apparatus consisted of a test chamber 30.5×25.4×30.5 cm (Coulbourn Instruments, Allenstown, Pa.). The top and two sides of the chamber were made of aluminum. The two other sides were made of transparent plastic. The box was dimly illuminated (xx lux). The floor consisted of stainless steel rods (5 mm dia, 1.68 cm between rods). Shock was delivered with a Precision Regulated Shocker (Model H12-16, Coulbourn Instruments). Rats were placed in a cage with a metal grid floor (grid dimensions). A mirror was placed on the opposite side of the chamber from the experimenter to facilitate observation. All rats were given a 2 min habituation period prior to the start of an experiment. Each rat was placed in the chamber for 2 min before a shock series was begun and after the grid floor had been cleaned with steel wool and water. Each shock pulse was 0.5 s in duration and the shocks were delivered at approximately 10 s intervals. Shock intensities were available from 0.05 to 4.0 mA in 20 steps arranged logarithmically. The full range was not used in determining thresholds. The ranges of intensities within which thresholds were to be found were estimated from preliminary observations. The midpoints of these ranges served as the beginning intensities in the experiments. A flinch was defined as elevation of one paw and jump as rapid movement of three or more paws, both responses required withdrawal from the floor. An adaptation of the "up-and-down" method for small samples was used for determining the order of presentation of shock intensities during each shock series.

The steps in the procedure were as follows: 1) The first series began with a shock intensity as close as possible to the flinch or jump threshold for the treatment being observed; 2) A series of trials was carried out such that the responses (flinch or jump) were followed by a decrease (0.1 $\log_{10}$ unit) in shock intensity and non-responses were followed by an increase (0.1 $\log_{10}$ unit) in shock intensity. Trials were continued in each series until a change in behavior occurred and were terminated four trials thereafter. The estimated median effective intensity ($EI_{50}$) was calculated by the formula $EI_{50}=X_f+kd$, where $X_f$=last intensity administered, k is the value in Table 1 of the Dixon reference (Dixon (1965) J. Am. Stat. Assoc. 60:47-55, and d is the log interval between shock intensities. Two series of shocks were performed to assess the flinch threshold, which were followed by two series of shocks to assess the jump threshold. This test controls for shock intensities given in the contextual fear conditioning behavioral paradigm and does not have separate results associated with it.

Example 4

Effect of Lasoperin™ on Speed of Processing

To assess the effect of Lasoperin™ on cognitive function a series of tests were performed over a 4 week period in cognitively intact individuals 35-65 years old. The individuals were treated with 300 mg/day of a Lasoperin™ formulation (80:20), which was prepared as described in Example 1. Measurement of cognitive performance was obtained using a series of web-based Cognitive Care tests which assess Psychomotor speed, Working Memory Speed (executive decision making, quickness & flexibility) and Immediate Memory (verbal & spatial memory processing). Before the study began, participants were required to practice the tests on two consecutive days to establish baseline performance. The data analysis compares baseline performance to performance post-treatment. The treated individuals were given weekly exams to determine if treatment with the dietary supplement resulted in a change in cognitive function. An analysis of the data compares baseline performance of treated individuals to those given a placebo over the same time period. Only subjects who completed the tests for the baseline and all dosing weeks were included in the analysis. Outliers who scored more than 2 standard deviations from the test mean, and who were not internally consistent with other test scores, were eliminated to exclude abnormal results that may be due to distractions or web/computer "glitches" that could invalidate the test session. Data was analyzed with a repeated measures analysis of variance (ANOVA) across days of testing, and comparisons between baseline and the final week of testing, with appropriate post hoc tests.

Psychomotor speed or physical reflex is a simple reaction time test that requires the subject to respond by pressing a key as quickly as possible after a figure appears on a computer screen. Overall performance for all ages on the psychomotor task was very stable and did not show any significant difference between groups for the mean, median or standard deviation measures ($p>0.05$). Thus, the Psychomotor speed test did not indicate any differences between treatment and control groups. There was however a generalized improvement in performance for all groups over the period of testing.

Working Memory Speed, a Complex Choice Reaction Time task, presents a word and a picture simultaneously and requires the person to determine if they are the same or different. A reversal cue is also presented randomly and requires the person to respond opposite to the correct response, so that a response to a correct pair would be no and visa versa. This task requires suppression or "inhibition of a learned response" and then a reversal ("task shifting") of the response contingency. The speed of switching from one task or one response mode to another is often equated with mental flexibility and higher-order cognitive processing, as well as superior decision-making. The cognitive aspects of this test can assess the executive cognitive function, including processing speed, sustained attention, cognitive fluidity and ability to correctly make rapid decisions in a complex and demanding cognitive task.

Immediate Memory is similar to the classic Sternberg task in which a string of stimulus "target" items to be remembered are followed by a "probe" item. The subject must determine if the probe item was a member of the previous target list. List length can be varied to provide an estimate of the short-term memory capacity of the individual. Both letters and spatial position are examined in this task.

The results are set forth in FIG. 3 which demonstrates that Lasoperin™ can increase cognitive processing (decision making) speed without impairing choice accuracy, thus, improving the rate of responding to cognitively demanding, or complex choice situations.

Example 5

Effect of Lasoperin™ on Focus and Attention as Measured by Reaction Time Standard Deviation To assess the effect of Lasoperin™ on cognitive function a series of tests were performed over a 4 week period in cognitively intact individuals 35-65 years old as described in Example 4. Reaction time standard deviation (RTSD) is often used as a measure of attention, and in the cognitive sciences, is typically considered to reflect processing efficiency and neural noise (Jensen). With reference to FIG. 4 it can be seen that there was significant improvement in RTSD over the 4 week testing period. That is there was a decrease in the standard deviation from baseline to week 4 for subjects administered Lasoperin™. Subjects administered the placebo also showed improvement, but not to the same degree. This suggests that the effect was due to improvement in consistency of task performance which was enhanced by treatment Lasoperin™, rather than simply learning to perform the test better. These results suggest that Lasoperin™ may increase sustained attention, improving the consistency of responding to cognitively demanding or complex choice situations.

Example 6

Inhibition of COX-1 and COX-2 by Lasoperin™

Measurement of the $IC_{50}$ of Lasoperin™ was performed using the following method. A cleavable, peroxide chromophore was included in the assay to visualize the peroxidase activity of each enzyme in the presence of arachidonic acid as a cofactor. Typically, the assays were performed in a 96-well format. Each inhibitor, taken from a 10 mg/mL stock in 100% DMSO, was tested in triplicate at room temperature using the following range of concentrations: 0, 0.1, 1, 5, 10, 20, 50, 100, and 500 µg/mL. To each well, 150 µL of 100 mM Tris-HCl, pH 7.5 was added together with 10 µL of 22 µM Hematin diluted in tris buffer, 10 µL of inhibitor diluted in DMSO, and 25 units of either COX-1 or COX-2 enzyme. The components were mixed for 10 seconds on a rotating platform, after which 20 µL of 2 mM N,N,N'N'-tetramethyl-p-phenylenediamine dihydrochloride (TMPD) and 20 µL of 1.1 mM AA was added to initiate the reaction. The plate was shaken for 10 seconds and then incubated for 5 minutes before reading the absorbance at 570 nm. The inhibitor concentration vs. percentage inhibition was plotted and the $IC_{50}$ determined by taking the half-maximal point along the isotherm and intersecting the concentration on the x-axis. The $IC_{50}$ was then normalized to the number of enzyme units in the assay. The dose response and $IC_{50}$ results for Lasoperin™ are provided in FIG. 5.

Example 7

Inhibition of 5-Lipoxygenase (5-LO) by Catechin Isolated from *A. catechu*

One of the most important pathways involved in the inflammatory response is produced by non-heme, iron-containing lipoxygenases (5-LO, 12-LO, and 15-LO), which catalyze the addition of molecular oxygen onto fatty acids such as arachidonic acid (AA) to produce the hydroperoxides 5-, 12- and 15-HPETE, which are then converted to leukotrienes. There were early indications that the flavan extract from *A. catechu* may provide some degree of 5-LO inhibition, thereby preventing the formation of 5-HPETE. A Lipoxygenase Inhibitor Screening Assay Kit (Cayman Chemical, Inc., Cat # 760700) was used to assess whether the purified flavan catechin from *A. catechu* directly inhibited 5-LO in vitro. The 15-LO from soybeans normally used in the kit was replaced with potato 5-LO after a buffer change from phosphate to a Tris-based buffer using microfiltration was performed. This assay detects the formation of hydroperoxides through an oxygen sensing chromagen. Briefly, the assay was performed in triplicate by adding 90 µL of 0.17 units/µL potato 5-LO, 20 µL of 1.1 mM AA, 100 µL of oxygen-sensing chromagen, and 1 µL of purified flavan inhibitor to final concentrations ranging from 0 to 500 µg/mL. The results are set forth in FIG. 6. The $IC_{50}$ for 5-LO inhibition from catechin was determined to be 1.38 µg/mL/unit of enzyme.

Example 8

Measurement of $LTB_4$ Levels Following Treatment with Lasoperin™

A Lasoperin™ formulation was prepared as outlined in Example 1, using a standardized Free-B-Ring flavonoid extract from *S. baicalensis* roots and a standardized flavan extract from *A. catechu* bark with a blending ratio of 80:20 Lasoperin™. The Lasoperin™ and ibuprofen, another known 5-LO inhibitor, were added to HT-29 cells, monocyte cell lines that express COX-1, COX-2 and 5-LO, at 3 µg/mL and incubated for 48 hours at 37° C. with 5% $CO_2$ in a humidified environment. Each treated cell line was then harvested by centrifugation and disrupted by gentle dounce homogenization in physiological lysis buffer. A competitive ELISA for $LTB_4$ ($LTB_4$; Neogen, Inc., Cat # 406110) was used to assess the effect of Lasoperin™ on newly synthesized levels of $LTB_4$ present in each cell line as a measure of Lasoperin's™ inhibitory effect on the 5-LO pathway. The assay was performed in duplicate by adding 160,000 to 180,000 cells per well in 6-well plates. The results are set forth in FIG. 7. As shown in FIG. 7, Lasoperin™ inhibited generation of 80% of the newly synthesized $LTB_4$ in HT-29 cells. Ibuprofen only showed a 20% reduction in the amount of $LTB_4$ over the same time period.

Example 9

Effect of Lasoperin™ on LPS-Induced Levels of TNFα and IL-10 in Peripheral Blood Monocytes Peripheral blood monocytes (PBMCs) from human blood donors were isolated using a Histopaque gradient (Sigma). The cells were then cultured in RPMI 1640 supplemented with 1% bovine serum albumin for approximately 12 hours before being treated with lipopolysaccharide (LPS) at increasing concentrations to induce inflammation in the presence of various concentrations of Lasoperin™ (80:20). The results are set forth in FIGS. 8-10.

Example 10

Differential Inhibition of cox-2 but not cox-1 Gene Expression by Lasoperin™ vs. Other NSAIDs To evaluate whether Lasoperin™ is operating on the genomic level, isolated human, peripheral blood monocytes (PBMCs) were stimulated with lipopolysaccharide (LPS), treated with Lasoperin™, celecoxib, ibuprofen or acetaminophen and the total RNA produced was then harvested and evaluated by semi-quantitative RT-qPCR. Specifically, the assay was constructed by adding 130,000 cells per well in 6-well plates. The cells were then stimulated with 10 ng/mL LPS and co-incubated with Lasoperin™ at 1, 3, 10, 30 and 100 µg/mL and celecoxib, ibuprofen and acetaminophen at 3 µg/mL for 18 hours at 37° C. with 5% $CO_2$ in a humidified environment. Each cell-treatment condition was then harvested by centrifugation and total RNA produced was isolated using TRIzol® reagent (Invitrogen™ Life Technologies, Cat # 15596-026) and the recommended TRIzol® reagent manufacturer protocol. Total RNA was reverse transcribed using Moloney Murine Leukemia Virus reverse transcriptase (M-MLV RT; Promega Corp., Cat # M1701) using random hexamers (Promega Corp., Cat#C1181). qPCR experiments were performed on an ABI Prism®7700 Sequence Detection System using pre-developed validated Assays-on-Demand products (AOD from Applied Biosystems, Inc., Cat # 4331182) for 18S rRNA internal standard and gene specific assays. Gene specific expression values were standardized to their respective 18S rRNA gene expression values (internal control) and then the no-LPS no-drug treatment condition normalized to 100. Treatment conditions are relative to this null condition. Lasoperin™ decreased normalized gene expression of cox-2 by over 100-fold while cox-1 normalized gene expression showed little variation. Under the same treatment conditions, normalized TNFα gene expression was decreased 6-fold and normalized IL-1β gene expression was decreased by over 100-fold. When PBMCs were treated with 3 µg/mL Lasoperin™, celecoxib, ibuprofen or acetaminophen, only Lasoperin™ did not increase gene expression of cox-2. This work has been coupled with ELISA-based assays to evaluate changes in protein levels as well as enzyme function assays to evaluate alterations in protein function. As a result of these studies, both genomic and proteomic coupled effects following treatment with Lasoperin™ have been demonstrated. Other studies cited in the literature have used protein specific methods to infer gene expression rather than show it directly. The results are set forth in FIGS. 11-13.

Example 11

Down-Regulation of mRNA for Key Inflammatory Proteins by Lasoperin™

PBMCs from human blood donors (obtained from a local blood bank) were isolated using a Histopaque gradient (Sigma). The cells were then cultured in RPMI 1640 supplemented with 1% bovine serum albumin for approximately 24 hours before being treated with LPS (10 µg/mL) and increasing concentrations Lasoperin™ (80:20). Specifically, the assay was constructed by adding 130,000 cells per well in 6-well plates. The cells were then stimulated with 10 µg/mL LPS and co-incubated with Lasoperin™ at 100 µg/mL for 18 hours at 37° C. with 5% $CO_2$ in a humidified environment. Each cell-treatment condition was then harvested by centrifugation and total RNA produced was isolated using TRIzol® reagent (Invitrogen™ Life Technologies, Cat # 15596-026) and the recommended TRIzol® reagent manufacturer protocol. Total RNA was reverse transcribed using Moloney Murine Leukemia Virus reverse transcriptase (M-MLV RT; Promega Corp., Cat # M1701) using random hexamers (Promega Corp., Cat#C1181). qPCR experiments were performed on an ABI Prism®7700 Sequence Detection System using pre-developed validated Assays-on-Demand products (AOD from Applied Biosystems, Inc., Cat # 4331182) for 18S rRNA internal standard and gene specific assays. Gene specific expression values were standardized to their respective cyclophylin A mRNA gene expression values (internal control) and then the no-LPS no-drug treatment condition normalized to 100. Treatment conditions are relative to this null condition. The results are set forth in FIG. 14.

With reference to FIG. 14 it can be seen that Lasoperin™ decreased normalized gene expression of cox-2 by an average of 3-fold while cox-1 normalized gene expression showed little variation. Under the same treatment conditions, normalized tnfa gene expression was decreased by an average of 3-fold, normalized il-1β gene expression was decreased by an average of 45-fold, and normalized il-6 gene expression was decreased by an average of 37-fold. Other studies cited in the literature have used protein specific methods to infer gene expression rather than show it directly as put forth in FIG. 14.

Example 12

Down-Regulation of Promoter Elements of Inflammatory Genes by Lasoperin™

The promoter regions for the inflammatory genes tnfα, il-1β, il-6 and cox-2 all contain NFκB binding sites which may account for down-regulation of gene expression when cells are treated with Lasoperin™. The cox-2 promoter region also contains a PPARγ responsive element (PPRE) which interacts with the retinoid X receptor transcription protein. Lasoperin™ down-regulates pparγ gene expression which presumably decreases PPARγ protein such that it cannot interact to stimulate cox-2 gene expression. Additionally, Lasoperin™ also down-regulates nfκb gene expression. Therefore, the compound hits two transcription factors that affect cox-2 gene expression and presumably COX-2 protein production. These promoter elements are shown in FIG. 15.

Example 13

Measurement of the Oxygen Radical Absorption Capacity (ORAC) of Lasoperin™

Lasoperin™ was tested for its Oxygen Radical Absorption Capacity (ORAC) relative to several well known food based antioxidants using the experimental procedures described in Cao et al. (1994) Free Radic. Biol. Med. 16:135-137 and Prior and Cao (1999) Proc. Soc. Exp. Biol. Med. 220:255-261. The ORAC analysis, which utilizes fluorescein as a fluorescent probe, provides a measure the capacity of antioxidants to scavenge for the peroxyl radical, which is one of the most common reactive oxygen species found in the body. $ORAC_{hydro}$ reflects the water-soluble antioxidant capacity and the $ORAC_{lipo}$ is the lipid soluble antioxidant capacity. Trolox, a water-soluble Vitamin E analog, is used as the calibration standard and the results are expressed as micromole Trolox equivalent (TE) per gram. Lasoperin™ has an $ORAC_{hydro}$ of 5,517 μmole TE/g and an $ORAC_{lipo}$ of 87 μmole TE/g for an $ORAC_{total}$ of 5,604 μmole TE/g. The results are set forth in the Table 2, which illustrates that Lasoperin™ has an ORAC comparable to Vitamin C and thus should decrease ROS levels in the body.

TABLE 2

ORAC of Lasoperin ™ Relative to Common Antioxidants.

| Sample ID | ORAC (μmole TE/g) |
|---|---|
| Vitamin C (aqueous Sol) | 5,000 |
| Vitamin E (lipid soluble) | 1,100 |
| Lasoperin Powder | 5,517 |
| Grape Concentrate | 133 |
| Cherry Concentrate | 79 |
| Cranberry Concentrate | 90 |
| Blueberry Concentrate | 125 |

Example 14

Quantification of the Mixture of Free-B-Ring Flavonoids and Flavans by Reverse Phase High Pressure Liquid Chromatography (HPLC) (Method 1)

Figure 16:
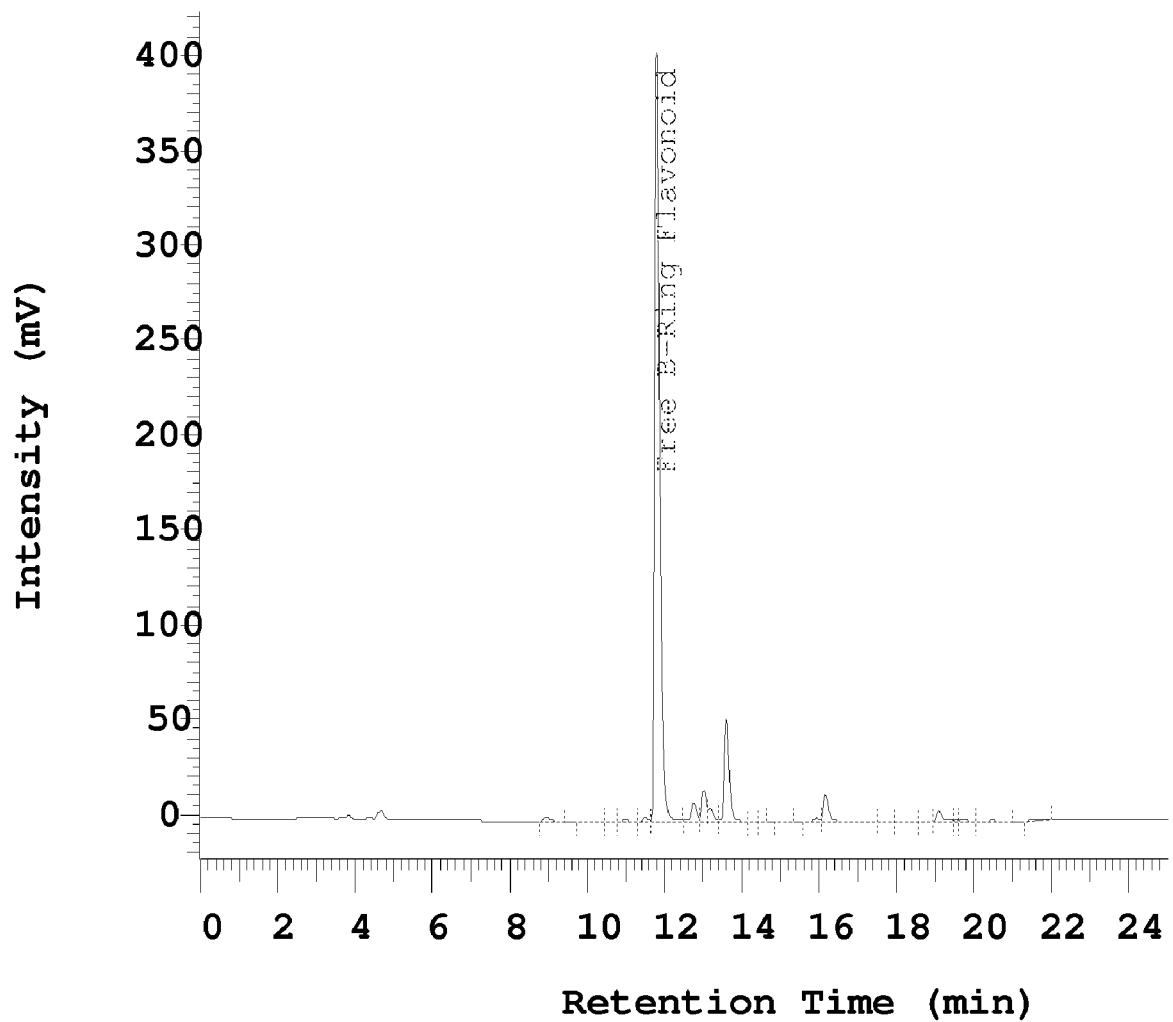
FIG. 16 illustrates the High Pressure Liquid Chromatography (HPLC) chromatogram of the mixture of Free-B-Ring flavonoids and flavans carried out under the conditions as described in Example 14. Using the described conditions the Free B-ring flavonoids eluted between 11 to 14 minutes and the flavans eluted between 3 to 5 minutes.

The mixture of Free-B-Ring flavonoids and flavans (20 μL of a 1.13 mg/mL standardized extract) in 80%:20% methanol:tetrahydrofuran was loaded onto a Phenomenex Luna C-18 column (250×4.6 mm, 5 μm bead size) and eluted with a 1.0 mL/min, linear 80% A to 20% A gradient for 19 minutes (A=0.1% (v/v) phosphoric acid; B=acetonitrile) at 35° C. As can be seen in FIG. 16, under these conditions the Free-B-Ring flavonoids (bacalein and bacalin) eluted as the major peak between 11 to 14 minutes and the flavans (catechins and epicatechins) eluted as the minor peak at approximately 3 to 5 minutes. The amount of Free-B-Ring flavonoids and flavans were determined by measuring the area under each curve and comparison with known standards.

Example 15

Quantification of the Mixture of Free-B-Ring Flavonoids and Flavans by Reverse Phase Isocratic HPLC (Method 2)

Figure 17:
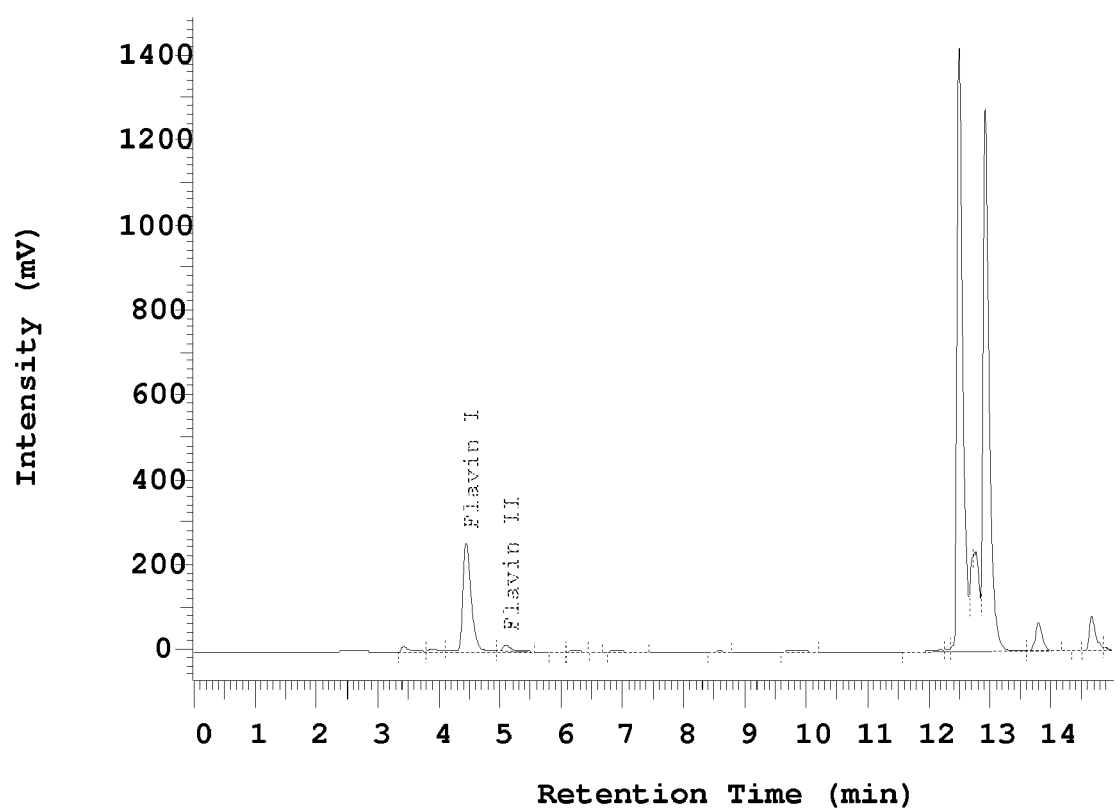
FIG. 17 depicts an HPLC chromatogram of the mixture of Free-B-Ring flavonoids and flavans carried out under the conditions as described in Example 14. Using the described conditions the two flavans (catechins and epicatechins) eluted between 4.5 to 5.5 minutes and the Free-B-Ring flavonoids (bacalein and bacalin) eluted between 12 and 13.5 minutes. Under the conditions described in Example 15, the separation is based upon differences in molar absorbtivity of the Free-B-Ring flavonoids and flavans.

The mixture of Free-B-Ring flavonoids and flavans (20 mL of a 3.55 mg/mL standardized extract) in 80%:20% methanol:water was loaded onto a Phenomenex Luna C-18 column (250×4.6 mm, 5 mm bead size) and eluted isocratically with 80% A (A=0.1% (v/v) phosphoric acid; B=acetonitrile) at 35° C. As can be seen in FIG. 17, under these conditions the two flavans (catechins and epicatechins) eluted between 4.5 to 5.5 minutes and the Free-B-Ring flavonoids (bacalein and bacalin) eluted between 12 and 13.5 minutes in the washout. Quantification of the flavan peaks was performed as described in Example 14.

What is claimed is:

1. A method for treating cyclooxygenase and lipoxygenase mediated inflammatory diseases and conditions related to memory and cognitive function, said method comprising administering to a host in need thereof an effective amount of a composition comprised of a mixture of an extract derived from *Scutellaria* enriched for Free-B-Ring flavonoids containing baicalin and an extract derived from *Acacia* enriched for flavans containing catechin or epicatechin wherein said cyclooxygenase and lipoxygenase mediated inflammatory diseases and conditions are selected from the group consisting of neurodegenerative disorders, stroke, dementia, Alzheimer's disease, Parkinson's disease, Huntington's disease, and Amyotrophic Lateral Sclerosis.

2. The method of claim 1 wherein the ratio of Free-B-Ring flavonoids to flavans in said composition is selected from the range of 99:1 Free-B-Ring flavonoids:flavans to 1:99 of Free-B-Ring flavonoids:flavans.

3. The method of claim 2 wherein the ratio of Free-B-Ring flavonoids:flavans in the composition of matter is about 80:20.

4. The method of claim 1 wherein said Free-B-Ring flavonoids and said flavans are isolated from a plant part selected from the group consisting of stems, stem barks, trunks, trunk barks, twigs, tubers, roots, root barks, young shoots, seeds, rhizomes, flowers and other reproductive organs, leaves and other aerial parts.

5. The method claim 1 wherein said flavans are isolated from a plant species selected from the group consisting of the *Acacia caechu, Acacia concinna, Acacia farnesiana, Acacia Senegal, Acacia speciosa, Acacia arabica, Acacia caesia, Acacia pennata, Acacia sinuate, Acacia Mearnsii, Acacia picnantha, Acacia dealbata, Acacia auriculiformis, Acacia holosercia,* and *Acacia mangium.*

6. The method of claim 1 wherein the composition is administered in a dosage selected from 0.001 to 200 mg/kg of body weight of said host.

7. The method of claim 1 wherein the administration is selected from the group consisting of oral, topical, suppository, intravenous, and intradermic, intragaster, intramusclar, intraperitoneal and intravenous administration.

8. The method of claim 1 wherein the composition is further comprised of a conventional excipient that is pharmaceutically, dermatologically and cosmetically suitable for topical application.

* * * * *